US011602440B2

(12) United States Patent
Zakelj

(10) Patent No.: US 11,602,440 B2
(45) Date of Patent: Mar. 14, 2023

(54) EXPANDABLE IMPLANT ASSEMBLY

(71) Applicant: LIFE SPINE, INC., Huntley, IL (US)

(72) Inventor: Paul Christopher Zakelj, Chicago, IL (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 16/912,242

(22) Filed: Jun. 25, 2020

(65) Prior Publication Data

US 2021/0401586 A1    Dec. 30, 2021

(51) Int. Cl.
*A61F 2/44* (2006.01)
*A61F 2/46* (2006.01)

(52) U.S. Cl.
CPC .......... *A61F 2/4425* (2013.01); *A61F 2/4455* (2013.01); *A61F 2/4611* (2013.01); *A61F 2002/443* (2013.01); *A61F 2220/0041* (2013.01); *A61F 2250/0006* (2013.01)

(58) Field of Classification Search
CPC .... A61F 2/4455; A61F 2/4465; A61F 2/4425; A61F 2002/443; A61F 2/447
See application file for complete search history.

(56) References Cited

U.S. PATENT DOCUMENTS

| 904,434 A | 11/1908 | Huff |
|---|---|---|
| 1,925,385 A | 9/1933 | Humes |
| 3,846,846 A | 11/1974 | Fischer |
| 4,466,426 A | 8/1984 | Blackman |
| 4,636,217 A | 1/1987 | Ogilvie et al. |
| 4,743,256 A | 5/1988 | Brantigan |
| 4,863,476 A | 9/1989 | Shepperd |
| 5,098,435 A | 3/1992 | Stednitz et al. |
| 5,192,327 A | 3/1993 | Brantigan |
| 5,236,460 A | 8/1993 | Barber |
| 5,390,683 A | 2/1995 | Pisharodi |
| 5,522,899 A | 6/1996 | Michelson |

(Continued)

FOREIGN PATENT DOCUMENTS

| CN | 102427769 A | 4/2012 |
|---|---|---|
| CN | 205866898 U | 1/2017 |

(Continued)

OTHER PUBLICATIONS

Bacfuse® Spinous Process Fusion Plate Surgical Technique, 2011, Pioneer Surgical, 12 pages.

(Continued)

*Primary Examiner* — Ellen C Hammond
(74) *Attorney, Agent, or Firm* — Foley & Lardner LLP

(57) ABSTRACT

An implant includes a first support, a second support rotatably coupled to the first support along a distal end of the implant, and a control assembly configured to move the implant between at least a first, collapsed orientation and a second, expanded orientation, the control assembly includes a control driver coupled to the first support and comprising a head and a shaft, the control driver configured to control relative movement between the first support and the second support, a control member configured to move along the (Continued)

shaft of the control driver, and a first linkage hingedly coupled to the control member and the second support, wherein movement of the control member causes the first support to move relative to the second support.

20 Claims, 12 Drawing Sheets

(56) References Cited

U.S. PATENT DOCUMENTS

| | | |
|---|---|---|
| 5,609,635 A | 3/1997 | Michelson |
| 5,645,599 A | 7/1997 | Samani |
| 5,658,335 A | 8/1997 | Allen |
| 5,658,337 A | 8/1997 | Kohrs et al. |
| 5,776,199 A | 7/1998 | Michelson |
| 5,836,948 A | 11/1998 | Zucherman et al. |
| 5,860,977 A | 1/1999 | Zucherman et al. |
| 5,876,404 A | 3/1999 | Zucherman et al. |
| 6,045,579 A | 4/2000 | Hochshuler et al. |
| 6,048,342 A | 4/2000 | Zucherman et al. |
| 6,068,630 A | 5/2000 | Zucherman et al. |
| 6,074,390 A | 6/2000 | Zucherman et al. |
| 6,080,193 A | 6/2000 | Hochshuler et al. |
| 6,113,638 A | 9/2000 | Williams et al. |
| 6,126,689 A | 10/2000 | Brett |
| 6,176,882 B1 | 1/2001 | Biedermann et al. |
| 6,183,471 B1 | 2/2001 | Zucherman et al. |
| 6,190,387 B1 | 2/2001 | Zucherman et al. |
| 6,235,030 B1 | 5/2001 | Zucherman et al. |
| 6,290,724 B1 | 9/2001 | Marino |
| 6,375,682 B1 | 4/2002 | Fleischmann et al. |
| 6,409,766 B1 | 6/2002 | Brett |
| 6,443,989 B1 | 9/2002 | Jackson |
| 6,443,990 B1 | 9/2002 | Aebi et al. |
| 6,447,544 B1 | 9/2002 | Michelson |
| 6,451,019 B1 | 9/2002 | Zucherman et al. |
| 6,491,724 B1 | 12/2002 | Ferree |
| 6,494,883 B1 | 12/2002 | Ferree |
| 6,537,320 B1 | 3/2003 | Michelson |
| 6,576,016 B1 | 6/2003 | Hochshuler et al. |
| 6,613,091 B1 | 9/2003 | Zdeblick et al. |
| 6,641,614 B1 | 11/2003 | Wagner et al. |
| 6,648,917 B2 | 11/2003 | Gerbec et al. |
| 6,685,742 B1 | 2/2004 | Jackson |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,706,070 B1 | 3/2004 | Wagner et al. |
| 6,752,832 B2 | 6/2004 | Neumann |
| 6,773,460 B2 | 8/2004 | Jackson |
| 6,796,983 B1 | 9/2004 | Zucherman et al. |
| 7,001,385 B2 | 2/2006 | Bonutti |
| 7,048,736 B2 | 5/2006 | Robinson et al. |
| 7,087,055 B2 | 8/2006 | Lim et al. |
| 7,101,375 B2 | 9/2006 | Zucherman et al. |
| 7,214,243 B2 | 5/2007 | Taylor |
| 7,217,291 B2 | 5/2007 | Zucherman et al. |
| 7,220,280 B2 | 5/2007 | Kast et al. |
| 7,250,055 B1 | 7/2007 | Vanderwalle |
| 7,473,276 B2 * | 1/2009 | Aebi ............... A61F 2/4425 623/17.15 |
| 7,503,933 B2 | 3/2009 | Michelson |
| 7,621,950 B1 | 11/2009 | Globerman et al. |
| 7,695,513 B2 | 4/2010 | Zucherman et al. |
| 7,727,280 B2 | 6/2010 | McLuen |
| 7,731,751 B2 | 6/2010 | Butler et al. |
| 7,789,914 B2 | 9/2010 | Michelson |
| D626,233 S | 10/2010 | Cipoletti et al. |
| 7,824,427 B2 | 11/2010 | Perez-Cruet et al. |
| 7,828,849 B2 | 11/2010 | Lim |
| 7,837,734 B2 | 11/2010 | Zucherman et al. |
| 7,850,733 B2 | 12/2010 | Baynham et al. |
| 7,854,766 B2 | 12/2010 | Moskowitz et al. |
| 7,867,277 B1 | 1/2011 | Tohmeh |
| 7,879,098 B1 | 2/2011 | Simmons, Jr. |
| 7,942,903 B2 | 5/2011 | Moskowitz et al. |
| 7,959,675 B2 | 6/2011 | Gately |
| 7,972,363 B2 | 7/2011 | Moskowitz et al. |
| 8,016,861 B2 | 9/2011 | Mitchell et al. |
| 8,021,430 B2 | 9/2011 | Michelson |
| 8,048,117 B2 | 11/2011 | Zucherman et al. |
| 8,062,375 B2 | 11/2011 | Glerum et al. |
| 8,071,007 B1 | 12/2011 | Teoh et al. |
| 8,105,382 B2 | 1/2012 | Olmos et al. |
| 8,187,332 B2 | 5/2012 | Mcluen |
| 8,231,656 B2 | 7/2012 | Lee et al. |
| 8,241,330 B2 | 8/2012 | Lamborne et al. |
| 8,241,364 B2 | 8/2012 | Hansell et al. |
| 8,252,060 B2 | 8/2012 | Hansell et al. |
| 8,257,370 B2 | 9/2012 | Moskowitz et al. |
| 8,267,939 B2 | 9/2012 | Cipoletti et al. |
| 8,303,663 B2 | 11/2012 | Jimenez et al. |
| 8,308,804 B2 | 11/2012 | Krueger |
| 8,343,190 B1 | 1/2013 | Mueller et al. |
| 8,353,913 B2 | 1/2013 | Moskowitz et al. |
| 8,353,963 B2 | 1/2013 | Glerum |
| 8,366,777 B2 | 2/2013 | Matthis et al. |
| 8,382,801 B2 | 2/2013 | Lamborne et al. |
| 8,382,842 B2 | 2/2013 | Greenhalgh et al. |
| 8,388,686 B2 | 3/2013 | Aebi et al. |
| 8,394,129 B2 | 3/2013 | Morgenstern Lopez |
| 8,398,713 B2 | 3/2013 | Weiman |
| 8,425,607 B2 | 4/2013 | Waugh et al. |
| 8,435,298 B2 | 5/2013 | Weiman |
| 8,444,696 B2 | 5/2013 | Michelson |
| 8,454,706 B2 | 6/2013 | De Beaubien |
| 8,491,659 B2 | 7/2013 | Weiman |
| 8,506,629 B2 | 8/2013 | Weiland |
| 8,518,120 B2 | 8/2013 | Glerum et al. |
| 8,529,628 B2 | 9/2013 | Marino et al. |
| 8,535,380 B2 | 9/2013 | Greenhalgh et al. |
| 8,551,173 B2 | 10/2013 | Lechmann et al. |
| 8,556,979 B2 | 10/2013 | Glerum et al. |
| 8,568,481 B2 | 10/2013 | Olmos et al. |
| 8,597,360 B2 | 12/2013 | Mcluen et al. |
| 8,628,578 B2 | 1/2014 | Miller et al. |
| 8,632,595 B2 | 1/2014 | Weiman |
| 8,641,764 B2 | 2/2014 | Gately |
| 8,641,766 B2 | 2/2014 | Donner et al. |
| 8,679,183 B2 | 3/2014 | Glerum et al. |
| 8,685,098 B2 | 4/2014 | Glerum et al. |
| 8,690,883 B2 | 4/2014 | Collins et al. |
| 8,702,798 B2 | 4/2014 | Matthis et al. |
| 8,709,086 B2 | 4/2014 | Glerum |
| 8,734,516 B2 | 5/2014 | Moskowitz et al. |
| 8,795,366 B2 | 8/2014 | Varela |
| 8,821,506 B2 | 9/2014 | Mitchell |
| 8,845,728 B1 | 9/2014 | Abdou |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 * | 11/2014 | Varela ............... A61F 2/447 623/17.16 |
| 8,906,095 B2 | 12/2014 | Christensen et al. |
| 8,926,704 B2 | 1/2015 | Glerum et al. |
| 8,936,641 B2 | 1/2015 | Cain |
| 8,940,052 B2 | 1/2015 | Lechmann et al. |
| 8,974,505 B2 | 3/2015 | Sawa et al. |
| 9,005,293 B2 | 4/2015 | Moskowitz et al. |
| 9,034,041 B2 | 5/2015 | Wolters et al. |
| 9,034,045 B2 | 5/2015 | Davenport et al. |
| 9,039,771 B2 | 5/2015 | Glerum et al. |
| 9,044,284 B2 | 6/2015 | Sweeney |
| 9,060,876 B1 | 6/2015 | To et al. |
| 9,101,487 B2 | 8/2015 | Petersheim |
| 9,119,730 B2 | 9/2015 | Glerum et al. |
| 9,125,757 B2 | 9/2015 | Weiman |

(56) References Cited

U.S. PATENT DOCUMENTS

| | | |
|---|---|---|
| 9,149,367 B2 | 10/2015 | Davenport et al. |
| 9,186,258 B2 | 11/2015 | Davenport et al. |
| 9,186,262 B2 | 11/2015 | Mcluen et al. |
| 9,198,772 B2 | 12/2015 | Weiman |
| 9,204,922 B2 | 12/2015 | Hooven |
| 9,204,972 B2 | 12/2015 | Weiman et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,216,098 B2 | 12/2015 | Trudeau et al. |
| 9,226,836 B2 | 1/2016 | Glerum |
| 9,233,009 B2 | 1/2016 | Gray et al. |
| 9,278,008 B2 | 3/2016 | Perloff et al. |
| 9,295,562 B2 | 3/2016 | Lechmann et al. |
| 9,301,854 B2 | 4/2016 | Moskowitz et al. |
| 9,358,123 B2 | 6/2016 | Mcluen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,370,434 B2 | 6/2016 | Weiman |
| 9,402,733 B1 | 8/2016 | To et al. |
| 9,402,738 B2 | 8/2016 | Niemiec et al. |
| 9,402,739 B2 | 8/2016 | Weiman et al. |
| 9,408,708 B2 | 8/2016 | Greenhalgh |
| 9,414,932 B2 | 8/2016 | Errico et al. |
| 9,421,111 B2 | 8/2016 | Baynham |
| 9,433,510 B2 | 9/2016 | Lechmann et al. |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |
| 9,474,622 B2 | 10/2016 | Mclaughlin et al. |
| 9,480,579 B2 | 11/2016 | Davenport et al. |
| 9,486,325 B2 | 11/2016 | Davenport et al. |
| 9,486,326 B2 | 11/2016 | Gahman et al. |
| 9,492,286 B2 | 11/2016 | Biedermann et al. |
| 9,492,287 B2 | 11/2016 | Glerum et al. |
| 9,492,289 B2 | 11/2016 | Davenport et al. |
| 9,510,954 B2 | 12/2016 | Glerum et al. |
| 9,517,144 B2 | 12/2016 | Mcatamney et al. |
| 9,532,821 B2 | 1/2017 | Moskowitz et al. |
| 9,532,883 B2 | 1/2017 | Mcluen et al. |
| 9,539,103 B2 | 1/2017 | Mclaughlin et al. |
| 9,539,108 B2 | 1/2017 | Glerum et al. |
| 9,554,918 B2 | 1/2017 | Weiman |
| 9,561,116 B2 | 2/2017 | Weiman et al. |
| 9,561,117 B2 | 2/2017 | Lechmann et al. |
| 9,572,677 B2 | 2/2017 | Davenport et al. |
| 9,579,124 B2 | 2/2017 | Gordon et al. |
| 9,585,765 B2 | 3/2017 | Niemiec et al. |
| 9,597,197 B2 | 3/2017 | Lechmann et al. |
| 9,597,200 B2 | 3/2017 | Glerum et al. |
| 9,603,713 B2 | 3/2017 | Moskowitz et al. |
| 9,610,174 B2 | 4/2017 | Wang et al. |
| 9,622,875 B2 | 4/2017 | Moskowitz et al. |
| 9,622,879 B2 | 4/2017 | Taylor et al. |
| 9,655,737 B2 | 5/2017 | Perloff et al. |
| 9,655,747 B2 | 5/2017 | Glerum et al. |
| 9,662,223 B2 | 5/2017 | Matthis et al. |
| 9,662,224 B2 | 5/2017 | Weiman et al. |
| 9,707,092 B2 | 7/2017 | Davenport et al. |
| 9,770,343 B2 | 9/2017 | Weiman |
| 9,782,265 B2 | 10/2017 | Weiman et al. |
| 9,801,733 B2 | 10/2017 | Wolters et al. |
| 9,814,601 B2 | 11/2017 | Moskowitz et al. |
| 9,833,336 B2 | 12/2017 | Davenport et al. |
| 9,839,528 B2 | 12/2017 | Weiman et al. |
| 9,848,993 B2 | 12/2017 | Moskowitz et al. |
| 9,848,997 B2 | 12/2017 | Glerum et al. |
| 9,848,998 B2 | 12/2017 | Moskowitz et al. |
| 9,855,151 B2 | 1/2018 | Weiman |
| 9,867,719 B2 | 1/2018 | Moskowitz et al. |
| 9,889,022 B2 | 2/2018 | Moskowitz et al. |
| 9,895,238 B2 | 2/2018 | Moskowitz et al. |
| 9,907,673 B2 | 3/2018 | Weiman et al. |
| 9,907,674 B2 | 3/2018 | Moskowitz et al. |
| 9,931,226 B2 | 4/2018 | Kurtaliaj et al. |
| 9,943,418 B2 | 4/2018 | Davenport et al. |
| 9,956,087 B2 | 5/2018 | Seifert et al. |
| 9,962,272 B1 | 5/2018 | Daffinson et al. |
| 9,968,462 B2 | 5/2018 | Weiman |
| 9,974,665 B2 | 5/2018 | Mcluen et al. |
| 9,980,822 B2 | 5/2018 | Perloff et al. |
| 9,980,823 B2 | 5/2018 | Matthis et al. |
| 9,987,143 B2 | 6/2018 | Robinson et al. |
| 10,004,607 B2 | 6/2018 | Weiman et al. |
| 10,016,283 B2 | 7/2018 | Mcluen et al. |
| 10,028,740 B2 | 7/2018 | Moskowitz et al. |
| 10,028,842 B2 | 7/2018 | Gray et al. |
| 10,034,772 B2 | 7/2018 | Glerum et al. |
| 10,034,773 B2 | 7/2018 | Mclaughlin et al. |
| 10,052,213 B2 | 8/2018 | Glerum et al. |
| 10,058,433 B2 | 8/2018 | Lechmann et al. |
| 10,064,742 B2 | 9/2018 | Taylor et al. |
| 10,076,367 B2 | 9/2018 | Moskowitz et al. |
| 10,076,423 B2 | 9/2018 | Miller et al. |
| 10,080,669 B2 | 9/2018 | Davenport et al. |
| 10,085,844 B2 | 10/2018 | Perloff et al. |
| 10,085,849 B2 | 10/2018 | Weiman et al. |
| 10,092,417 B2 | 10/2018 | Weiman et al. |
| 10,092,422 B2 | 10/2018 | Mcluen et al. |
| 10,098,757 B2 | 10/2018 | Logan et al. |
| 10,098,758 B2 | 10/2018 | Matthews et al. |
| 10,098,759 B2 | 10/2018 | Weiman |
| 10,105,239 B2 | 10/2018 | Niemiec et al. |
| 10,111,760 B2 | 10/2018 | Knapp et al. |
| 10,117,754 B2 | 11/2018 | Davenport et al. |
| 10,137,001 B2 | 11/2018 | Weiman |
| 10,137,007 B2 * | 11/2018 | Dewey .............. A61F 2/447 |
| 10,143,500 B2 | 12/2018 | Niemiec et al. |
| 10,143,569 B2 | 12/2018 | Weiman et al. |
| 10,154,911 B2 * | 12/2018 | Predick ............ A61F 2/4455 |
| 10,159,583 B2 | 12/2018 | Dietzel et al. |
| 10,213,321 B2 | 2/2019 | Knapp et al. |
| 10,219,913 B2 | 3/2019 | Matthews et al. |
| 10,226,359 B2 | 3/2019 | Glerum et al. |
| 10,251,643 B2 | 4/2019 | Moskowitz et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,292,830 B2 | 5/2019 | Mcluen et al. |
| 10,299,934 B2 | 5/2019 | Seifert et al. |
| 10,307,268 B2 | 6/2019 | Moskowitz et al. |
| 10,350,085 B2 | 7/2019 | Glerum et al. |
| 10,376,386 B2 | 8/2019 | Moskowitz et al. |
| 10,383,741 B2 | 8/2019 | Butler et al. |
| 10,420,654 B2 | 9/2019 | Logan et al. |
| 10,426,632 B2 | 10/2019 | Butler et al. |
| 10,426,633 B2 | 10/2019 | Moskowitz et al. |
| 10,433,977 B2 | 10/2019 | Lechmann et al. |
| 10,449,058 B2 | 10/2019 | Lechmann et al. |
| 10,470,894 B2 | 11/2019 | Foley et al. |
| 10,478,319 B2 | 11/2019 | Moskowitz et al. |
| 10,512,550 B2 | 12/2019 | Bechtel et al. |
| 10,531,895 B2 | 1/2020 | Weiman et al. |
| 10,575,966 B2 | 3/2020 | Logan et al. |
| 10,617,533 B2 | 4/2020 | Glerum et al. |
| 10,624,761 B2 | 4/2020 | Davenport et al. |
| 10,639,166 B2 | 5/2020 | Weiman et al. |
| 10,682,240 B2 | 6/2020 | Mcluen et al. |
| 10,702,393 B2 | 7/2020 | Davenport et al. |
| 10,709,569 B2 | 7/2020 | Mclaughlin et al. |
| 10,709,571 B2 | 7/2020 | Iott et al. |
| 10,709,573 B2 | 7/2020 | Weiman et al. |
| 10,709,574 B2 | 7/2020 | Mcluen et al. |
| 10,722,379 B2 | 7/2020 | Mclaughlin et al. |
| 10,729,560 B2 | 8/2020 | Baker et al. |
| 10,729,562 B2 | 8/2020 | Knapp et al. |
| 10,736,754 B2 | 8/2020 | Mcluen et al. |
| 10,758,367 B2 | 9/2020 | Weiman et al. |
| 10,765,528 B2 | 9/2020 | Weiman et al. |
| 10,772,737 B2 | 9/2020 | Gray et al. |
| 10,779,957 B2 | 9/2020 | Weiman et al. |
| 10,786,364 B2 | 9/2020 | Davenport et al. |

(56) References Cited

U.S. PATENT DOCUMENTS

| | | |
|---|---|---|
| 10,799,368 B2 | 10/2020 | Glerum et al. |
| 10,835,387 B2 | 11/2020 | Weiman et al. |
| 10,842,644 B2 | 11/2020 | Weiman et al. |
| 10,869,768 B2 | 12/2020 | Weiman et al. |
| 10,874,522 B2 | 12/2020 | Weiman |
| 10,874,523 B2 | 12/2020 | Weiman et al. |
| 10,925,752 B2 | 2/2021 | Weiman |
| 10,940,014 B2 | 3/2021 | Greenhalgh |
| 10,973,649 B2 | 4/2021 | Weiman et al. |
| 11,020,239 B2 * | 6/2021 | Miller .................... A61F 2/447 |
| 11,051,951 B2 | 7/2021 | Robinson et al. |
| 11,065,128 B2 | 7/2021 | Zappacosta et al. |
| 2002/0010472 A1 | 1/2002 | Kuslich et al. |
| 2002/0029084 A1 | 3/2002 | Paul et al. |
| 2002/0128716 A1 | 9/2002 | Cohen et al. |
| 2002/0143343 A1 | 10/2002 | Castro |
| 2002/0143399 A1 | 10/2002 | Sutcliffe |
| 2003/0004576 A1 | 1/2003 | Thalgott |
| 2003/0040746 A1 | 2/2003 | Mitchell et al. |
| 2003/0040802 A1 | 2/2003 | Errico et al. |
| 2003/0176926 A1 | 9/2003 | Boehm et al. |
| 2003/0236520 A1 | 12/2003 | Lim et al. |
| 2004/0073213 A1 | 4/2004 | Serhan et al. |
| 2004/0153156 A1 | 8/2004 | Cohen et al. |
| 2004/0167625 A1 | 8/2004 | Beyar et al. |
| 2004/0204747 A1 | 10/2004 | Kemeny et al. |
| 2004/0225292 A1 | 11/2004 | Sasso et al. |
| 2004/0254643 A1 | 12/2004 | Jackson |
| 2005/0033437 A1 | 2/2005 | Bao et al. |
| 2005/0070911 A1 | 3/2005 | Carrison et al. |
| 2005/0107800 A1 | 5/2005 | Frankel et al. |
| 2005/0119747 A1 | 6/2005 | Fabris Monterumici |
| 2005/0131536 A1 | 6/2005 | Eisermann et al. |
| 2005/0143827 A1 | 6/2005 | Globerman et al. |
| 2005/0177235 A1 | 8/2005 | Baynham et al. |
| 2005/0177236 A1 | 8/2005 | Mathieu et al. |
| 2005/0222681 A1 | 10/2005 | Richley et al. |
| 2005/0228391 A1 | 10/2005 | Levy et al. |
| 2005/0261769 A1 | 11/2005 | Moskowitz et al. |
| 2005/0278036 A1 | 12/2005 | Leonard et al. |
| 2006/0030943 A1 | 2/2006 | Peterman |
| 2006/0036258 A1 | 2/2006 | Zucherman et al. |
| 2006/0084988 A1 | 4/2006 | Kim |
| 2006/0089715 A1 | 4/2006 | Truckai et al. |
| 2006/0089718 A1 | 4/2006 | Zucherman et al. |
| 2006/0095136 A1 | 5/2006 | McLuen |
| 2006/0189999 A1 | 8/2006 | Zwirkoski |
| 2006/0241601 A1 | 10/2006 | Trautwein et al. |
| 2006/0253201 A1 | 11/2006 | McLuen |
| 2006/0264938 A1 | 11/2006 | Zucherman et al. |
| 2006/0265077 A1 | 11/2006 | Zwirkoski |
| 2007/0072475 A1 | 3/2007 | Justin et al. |
| 2007/0142915 A1 | 6/2007 | Altarac et al. |
| 2007/0244485 A1 | 10/2007 | Greenhalgh et al. |
| 2007/0270968 A1 | 11/2007 | Baynham et al. |
| 2008/0114367 A1 | 5/2008 | Meyer |
| 2008/0114453 A1 | 5/2008 | Francis |
| 2008/0114456 A1 | 5/2008 | Dewey et al. |
| 2008/0140085 A1 | 6/2008 | Gately et al. |
| 2008/0140207 A1 | 6/2008 | Olmos et al. |
| 2008/0147193 A1 | 6/2008 | Matthis et al. |
| 2008/0161818 A1 | 7/2008 | Kloss et al. |
| 2008/0177391 A1 | 7/2008 | Mitchell et al. |
| 2008/0183211 A1 | 7/2008 | Lamborne et al. |
| 2008/0288077 A1 | 11/2008 | Reo et al. |
| 2008/0312741 A1 | 12/2008 | Lee et al. |
| 2009/0005872 A1 | 1/2009 | Moumene et al. |
| 2009/0062915 A1 | 3/2009 | Kohm et al. |
| 2009/0105832 A1 | 4/2009 | Allain et al. |
| 2009/0192553 A1 | 7/2009 | Maguire et al. |
| 2009/0198339 A1 | 8/2009 | Kleiner et al. |
| 2009/0222099 A1 | 9/2009 | Liu et al. |
| 2009/0312837 A1 | 12/2009 | Eisermann et al. |
| 2010/0103344 A1 | 4/2010 | Wang et al. |
| 2010/0179655 A1 | 7/2010 | Hansell et al. |
| 2010/0204795 A1 | 8/2010 | Greenhalgh |
| 2010/0211176 A1 | 8/2010 | Greenhalgh |
| 2010/0241167 A1 | 9/2010 | Taber et al. |
| 2010/0249937 A1 | 9/2010 | Blain et al. |
| 2010/0286777 A1 | 11/2010 | Errico et al. |
| 2011/0022090 A1 | 1/2011 | Gordon et al. |
| 2011/0066186 A1 | 3/2011 | Boyer et al. |
| 2011/0071635 A1 | 3/2011 | Zhang et al. |
| 2011/0077738 A1 | 3/2011 | Ciupik et al. |
| 2011/0144692 A1 | 6/2011 | Saladin et al. |
| 2011/0144755 A1 | 6/2011 | Baynham et al. |
| 2011/0166654 A1 | 7/2011 | Gately |
| 2011/0172709 A1 | 7/2011 | Lyons et al. |
| 2011/0172774 A1 | 7/2011 | Varela |
| 2011/0178599 A1 | 7/2011 | Brett |
| 2011/0184468 A1 | 7/2011 | Metcalf et al. |
| 2011/0196494 A1 | 8/2011 | Yedlicka et al. |
| 2011/0224731 A1 | 9/2011 | Smisson et al. |
| 2011/0282453 A1 | 11/2011 | Greenhalgh et al. |
| 2011/0301711 A1 | 12/2011 | Palmatier et al. |
| 2011/0319997 A1 | 12/2011 | Glerum et al. |
| 2012/0010717 A1 | 1/2012 | Spann |
| 2012/0016418 A1 | 1/2012 | Chin et al. |
| 2012/0022652 A1 | 1/2012 | Berger et al. |
| 2012/0035730 A1 | 2/2012 | Spann |
| 2012/0046748 A1 | 2/2012 | Weiman |
| 2012/0059472 A1 | 3/2012 | Weiman |
| 2012/0059474 A1 | 3/2012 | Weiman |
| 2012/0071978 A1 | 3/2012 | Suedkamp et al. |
| 2012/0109203 A1 | 5/2012 | Dryer et al. |
| 2012/0185049 A1 | 7/2012 | Varela |
| 2012/0221051 A1 | 8/2012 | Robinson |
| 2012/0226357 A1 | 9/2012 | Varela |
| 2012/0330422 A1 | 12/2012 | Weiman |
| 2013/0023993 A1 | 1/2013 | Weiman |
| 2013/0023994 A1 | 1/2013 | Glerum |
| 2013/0085572 A1 | 4/2013 | Glerum et al. |
| 2013/0103156 A1 | 4/2013 | Packer et al. |
| 2013/0116793 A1 | 5/2013 | Kloss |
| 2013/0158663 A1 | 6/2013 | Miller et al. |
| 2013/0158664 A1 * | 6/2013 | Palmatier ................ A61F 2/447 |
| | | 623/17.16 |
| 2013/0158668 A1 | 6/2013 | Nichols et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2014/0067071 A1 | 3/2014 | Weiman et al. |
| 2014/0148904 A1 | 5/2014 | Robinson |
| 2014/0163683 A1 | 6/2014 | Seifert et al. |
| 2014/0188224 A1 | 7/2014 | Dmuschewsky |
| 2014/0236296 A1 | 8/2014 | Wagner et al. |
| 2014/0249629 A1 | 9/2014 | Moskowitz et al. |
| 2014/0277461 A1 | 9/2014 | Nebosky et al. |
| 2014/0277473 A1 | 9/2014 | Perrow |
| 2014/0277500 A1 | 9/2014 | Logan et al. |
| 2014/0288653 A1 | 9/2014 | Chen |
| 2014/0343678 A1 * | 11/2014 | Suddaby ............... A61F 2/4611 |
| | | 623/17.16 |
| 2015/0012097 A1 | 1/2015 | Ibarra et al. |
| 2015/0066145 A1 | 3/2015 | Rogers et al. |
| 2015/0100128 A1 | 4/2015 | Glerum et al. |
| 2015/0112438 A1 | 4/2015 | Mclean |
| 2015/0173917 A1 | 6/2015 | Radcliffe et al. |
| 2015/0230931 A1 | 8/2015 | Greenhalgh |
| 2015/0351928 A1 | 12/2015 | Butler et al. |
| 2015/0374507 A1 | 12/2015 | Wolters et al. |
| 2016/0051377 A1 | 2/2016 | Weiman et al. |
| 2016/0089247 A1 | 3/2016 | Nichols et al. |
| 2016/0120660 A1 | 5/2016 | Melkent et al. |
| 2016/0242927 A1 | 8/2016 | Seifert et al. |
| 2016/0310291 A1 | 10/2016 | Greenhalgh |
| 2016/0361177 A1 | 12/2016 | Biedermann et al. |
| 2016/0367377 A1 * | 12/2016 | Faulhaber ............. A61F 2/4455 |
| 2017/0014244 A1 | 1/2017 | Seifert et al. |
| 2017/0056197 A1 | 3/2017 | Weiman et al. |
| 2017/0172756 A1 | 6/2017 | Faulhaber |
| 2017/0216036 A1 | 8/2017 | Cordaro |
| 2017/0224504 A1 | 8/2017 | Butler et al. |
| 2017/0224505 A1 | 8/2017 | Butler et al. |

(56) References Cited

U.S. PATENT DOCUMENTS

| | | |
|---|---|---|
| 2017/0246006 A1* | 8/2017 | Carnes .................. A61F 2/4611 |
| 2017/0258605 A1 | 9/2017 | Blain et al. |
| 2017/0281432 A1 | 10/2017 | Glerum et al. |
| 2017/0296352 A1 | 10/2017 | Richerme et al. |
| 2017/0333198 A1 | 11/2017 | Robinson |
| 2017/0333199 A1 | 11/2017 | Sharifi-Mehr et al. |
| 2017/0333200 A1 | 11/2017 | Arnin |
| 2017/0348116 A1 | 12/2017 | Weiman |
| 2017/0367842 A1 | 12/2017 | Predick et al. |
| 2018/0014947 A1 | 1/2018 | Baynham |
| 2018/0042732 A1 | 2/2018 | Seifert et al. |
| 2018/0049885 A1 | 2/2018 | Weiman et al. |
| 2018/0055652 A1 | 3/2018 | Davenport et al. |
| 2018/0243107 A1 | 8/2018 | Foley et al. |
| 2018/0256359 A1 | 9/2018 | Greenhalgh |
| 2018/0303621 A1 | 10/2018 | Brotman et al. |
| 2018/0318101 A1 | 11/2018 | Engstrom |
| 2018/0325693 A1 | 11/2018 | Weiman et al. |
| 2018/0360616 A1 | 12/2018 | Luu |
| 2019/0021871 A1 | 1/2019 | Baynham |
| 2019/0133779 A1 | 5/2019 | Mclaughlin et al. |
| 2019/0133784 A1 | 5/2019 | Gunn et al. |
| 2019/0201210 A1 | 7/2019 | Besaw et al. |
| 2019/0254836 A1 | 8/2019 | Cowan et al. |
| 2019/0254838 A1 | 8/2019 | Miller et al. |
| 2019/0298524 A1 | 10/2019 | Lauf et al. |
| 2019/0307577 A1 | 10/2019 | Predick et al. |
| 2019/0314168 A1 | 10/2019 | Faulhaber |
| 2019/0328540 A1 | 10/2019 | Seifert et al. |
| 2019/0374348 A1 | 12/2019 | Butler et al. |
| 2019/0388232 A1 | 12/2019 | Purcell et al. |
| 2019/0388238 A1 | 12/2019 | Lechmann et al. |
| 2020/0054461 A1 | 2/2020 | Marrocco et al. |
| 2020/0360153 A1 | 11/2020 | Weiman et al. |
| 2021/0015627 A1 | 1/2021 | Weiman et al. |
| 2021/0045892 A1 | 2/2021 | Rogers et al. |
| 2021/0113349 A1 | 4/2021 | Weiman et al. |
| 2021/0137699 A1 | 5/2021 | Jang et al. |
| 2021/0259849 A1 | 8/2021 | Robinson et al. |
| 2022/0133495 A1 | 5/2022 | Glerum et al. |

FOREIGN PATENT DOCUMENTS

| | | |
|---|---|---|
| DE | 94 07 806 U1 | 7/1994 |
| DE | 20314708 U1 | 11/2003 |
| EP | 2 777 633 A2 | 9/2014 |
| EP | 3 031 424 A1 | 6/2016 |
| EP | 3 245 982 | 11/2017 |
| EP | 3 479 799 A1 | 5/2019 |
| FR | 2717068 A1 | 4/1996 |
| FR | 2727003 B1 | 4/1997 |
| GB | 0 284 462 A | 2/1928 |
| KR | 200290058 Y1 | 9/2002 |
| KR | 100905962 B1 | 7/2009 |
| WO | WO-95/31158 A1 | 11/1995 |
| WO | WO-99/26562 A1 | 6/1999 |
| WO | WO-00/44319 A1 | 8/2000 |
| WO | WO-02/44319 A1 | 6/2002 |
| WO | WO-2004/052245 | 6/2004 |
| WO | WO-2005/009299 A1 | 2/2005 |
| WO | WO-2006/102485 | 9/2006 |
| WO | WO-2006/1 05437 A2 | 10/2006 |
| WO | WO-2009/124269 A1 | 10/2009 |
| WO | WO-2010/148112 | 12/2010 |
| WO | WO-2012/121726 A1 | 9/2012 |
| WO | WO-2014/134590 A1 | 9/2014 |
| WO | WO-2014/165319 A1 | 10/2014 |
| WO | WO-2015/009793 A1 | 1/2015 |
| WO | WO-2015/063721 A1 | 5/2015 |
| WO | WO-2015/085111 A1 | 6/2015 |
| WO | WO-201 6/077610 A1 | 5/2016 |
| WO | WO-201 6/127139 A1 | 8/2016 |
| WO | WO-201 7/027873 A1 | 2/2017 |
| WO | WO-2017/027277 A1 | 2/2017 |
| WO | WO-201 7/066463 A1 | 4/2017 |
| WO | WO-2018/049227 A1 | 3/2018 |
| WO | WO-2018/200507 A1 | 11/2018 |
| WO | WO-2018/200530 A1 | 11/2018 |
| WO | WO2019/0014139 A1 | 1/2019 |
| WO | WO-2019/014139 A1 | 1/2019 |
| WO | WO-2019/241687 A1 | 12/2019 |

OTHER PUBLICATIONS

Extended European Search Report for European Application No. 14159101.6, dated Jun. 18, 2014, 6 pages.

Extended European Search Report for European Application No. 16169890.7, dated Oct. 21, 2016, 7 pages.

Foreign Action other than Search Report on EP 06740268.5 dated Jan. 2, 2020.

Foreign Action other than Search Report on PCT PCT/US2018/029120 dated Nov. 7, 2019.

Foreign Action other than Search Report on PCT PCT/US2018/029149 dated Nov. 7, 2019.

Foreign Action other than Search Report on PCT PCT/US2018/041306 dated Jan. 23, 2020.

Foreign Search Report on PCT PCT/US2019/037275 dated Sep. 24, 2019.

International Preliminary Report on Patentability for Application No. PCT/US06/12060 dated Sep. 30, 2007, 3 pages.

International Search Report and Written Opinion for International Application No. PCT/US2006/012060, dated Apr. 5, 2007, 4 pages.

International Search Report and Written Opinion for International Application No. PCT/US2012/057324, dated Dec. 20, 2012, 10 pages.

International Search Report for International Application No. PCT/US2018/029120, dated Jun. 28, 2018, 17 pages.

International Search Report for International Application No. PCT/US2018/029149, dated Jun. 25, 2018, 13 pages.

Search Report for International Application No. PCT/US2018/041306, dated Sep. 28, 2018, 12 pages.

Written Opinion of the International Searching Authority for Application No. PCT/US06/12060, dated Apr. 5, 2007, 3 pages.

International Search Report and Written Opinion in PCT/US2021/033832 dated Sep. 17, 2021.

International Search Report and Written Opinion in PCT PCT/US2021/030261 dated Aug. 31, 2021 (18 pages).

International Search Report and Written Opinion in PCT/US2021/031596 dated Sep. 28, 2021 (12 pages).

International Search Report and Written Opinion on PCT/US2020/036809 dated Sep. 14, 2020, 12 pages.

International Search Report and Written Opinion received for Life Spine, Inc. for PCT app. PCT/US2021/026606 dated Jul. 15, 2021, 20 pages.

International Search Report and Written Opinion received for Life Spine, Inc., for PCT app. No. PCT/US2021026610 dated Jul. 20, 2021, 18 pages.

International Search Report on PCT/US2020/037020, dated Sep. 29, 2020, 20 pages.

"MectaLIF Oblique & Posterior Intervertebral Body Fusion Device." Brochure. 2004, Medacta International, San Pietro, Switzerland.

"Webster's II New College Dictionary." Excerpts. 2005, Houghton Mifflin Co., p. 992.

"Wedge." Encyclopedia Brittanica. Aug. 14, 2008. britannica.com/print/article/638734.

Folman, et al., "Posterior Lumbar Interbody Fusion for Degenerative Disc Disease Using a Minimally Invasive B-Twin Expandable Spinal Spacer." Journal of Spinal Disorders & Techniques. 2003, vol. 16, No. 5, pp. 455-460.

Kambin, P., et al., "Arthroscopic Discectomy of the Lumbar Spine." Clinical Orthopaedics and Related Research. Apr. 1997, No. 337, pp. 49-57.

Kim, D., et al. "Posterior Lumbar Interbody Fusion Using a Unilateral Single Cage and a Local Morselized Bone Graft in the Degenerative Lumbar Spine." Clinics in Orthopedic Surgery. 2009, vol. 1, No. 4, pp. 214-221.

(56) References Cited

OTHER PUBLICATIONS

Kim, Y, et al., "Clinical Applications of the Tubular Retractor on Spinal Disorders." Journal of Korean Neurosurgery, Nov. 2007, No. 42, pp. 244-250.

Moore, J., et al., "Mechanics Map—Wedges." Aug. 20, 2022, mechanicsmap.psu.edu/websites/7_friction/7-3_wedges/wedges.

Peltier, L. "Orthopedics: A History and Iconography" 1993, Norman Publishing, San Francisco, CA.

Sasso, R., et al., "Anterior Lumbar Interbody Fusion." Surgical Management of Low Back Pain. 2009, Chapter 10, pp. 87-95.

Schizas, C., "Spinal Fusion: Techniques Results and Limitations." European Cells and Materials. 2005, vol. 10, Suppl. 3, p. 1.

Tsuang, Y., et al., "Comparison of cage application modality in posterior lumbar interbody fusion with posterior instrumentation—A finite element study." Medical Engineering & Physics 31. 2009, pp. 565-570.

Virk, S., et al. "History of Spinal Fusion: Where We Came from and Where We Are Going." Current Concepts in Spinal Fusion. HSS Journal, 2020, No. 16, pp. 137-142.

Xiao, Y, et al., "Unilateral Transforaminal Lumbar Interbody Fusion: a Review of the Technique, Indications and Graft Materials." The Journal of International Medical Research. 2009, No. 37, pp. 908-917.

\* cited by examiner

EXPANDABLE IMPLANT ASSEMBLY

BACKGROUND

The present disclosure generally relates to implants. More specifically, the present application relates to expandable implants and devices, including spinal interbody and intravertebral body devices, and vertebral interbody and intravertebral devices that are expandable after spinal placement thereof.

Many people contend with spine or other issues as a result of age, disease, and trauma, as well as congenital and acquired complications and conditions. While some of these issues can be alleviated without surgery, other issues necessitate surgery. Spinal fusion may be recommended for conditions such as spondylolistheses, degenerative disc disease, or recurrent disc herniation, and is designed to create solid bone between adjacent vertebrae, thereby eliminating any movement between the bones. A spinal fusion uses an implant or device known as an interbody cage or spacer along with bone graft and/or bone graft substitute that is inserted into the disc space between adjacent vertebrae from one side of the spine. Typically, additional surgical hardware (implants) such as pedicle screws and rods or plates are attached to the back of the vertebrae. As the bone graft heals, it fuses the adjacent vertebrae to form one long vertebra.

Fusion cages, as well as other types of implants, bodies and/or devices, are frequently utilized in spinal surgery inside a vertebra (intravertebral) and/or between vertebrae of a patient (interbody), or adjacent other bone bodies. With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posterolaterally.

SUMMARY

In some embodiments, an implant includes a first support, a second support rotatably coupled to the first support along a distal end of the implant, and a control assembly configured to move the implant between at least a first, collapsed orientation and a second, expanded orientation. The control assembly includes a control driver coupled to the first support and including a head and a shaft, the control driver configured to control relative movement between the first support and the second support, a control member configured to move along the shaft of the control driver, and a first linkage hingedly coupled to the control member and the second support, wherein movement of the control member causes the first support to move relative to the second support.

In some embodiments, an implant includes an upper support a lower support rotatably coupled to the upper support, and a control assembly configured to expand the implant between at least a first, collapsed orientation and a second, expanded orientation, the control assembly including a first linkage hingedly coupled to the lower support, wherein manipulation of the control assembly causes movement of the first linkage relative to the upper support and the lower support.

In some embodiments, an expandable implant includes an upper support having a top surface configured to engage a first portion of bone, a lower support having a bottom surface configured to engage a second portion of bone, the lower support hingedly coupled to the upper support at a rear portion of the expandable implant, wherein the top surface of the upper support and the bottom surface of the lower support define an angle, and a control assembly including a linkage coupled to at least one of the upper support and the lower support, the control assembly configured to control movement between the upper support and the lower support between at least a first, collapsed orientation and a second, expanded orientation, wherein manipulation of the control assembly causes the angle to change.

BRIEF DESCRIPTION OF THE FIGURES

The features of the subject matter disclosed herein will be better understood by reference to the accompanying drawings which illustrate the subject matter disclosed herein, wherein.

Figure 1:
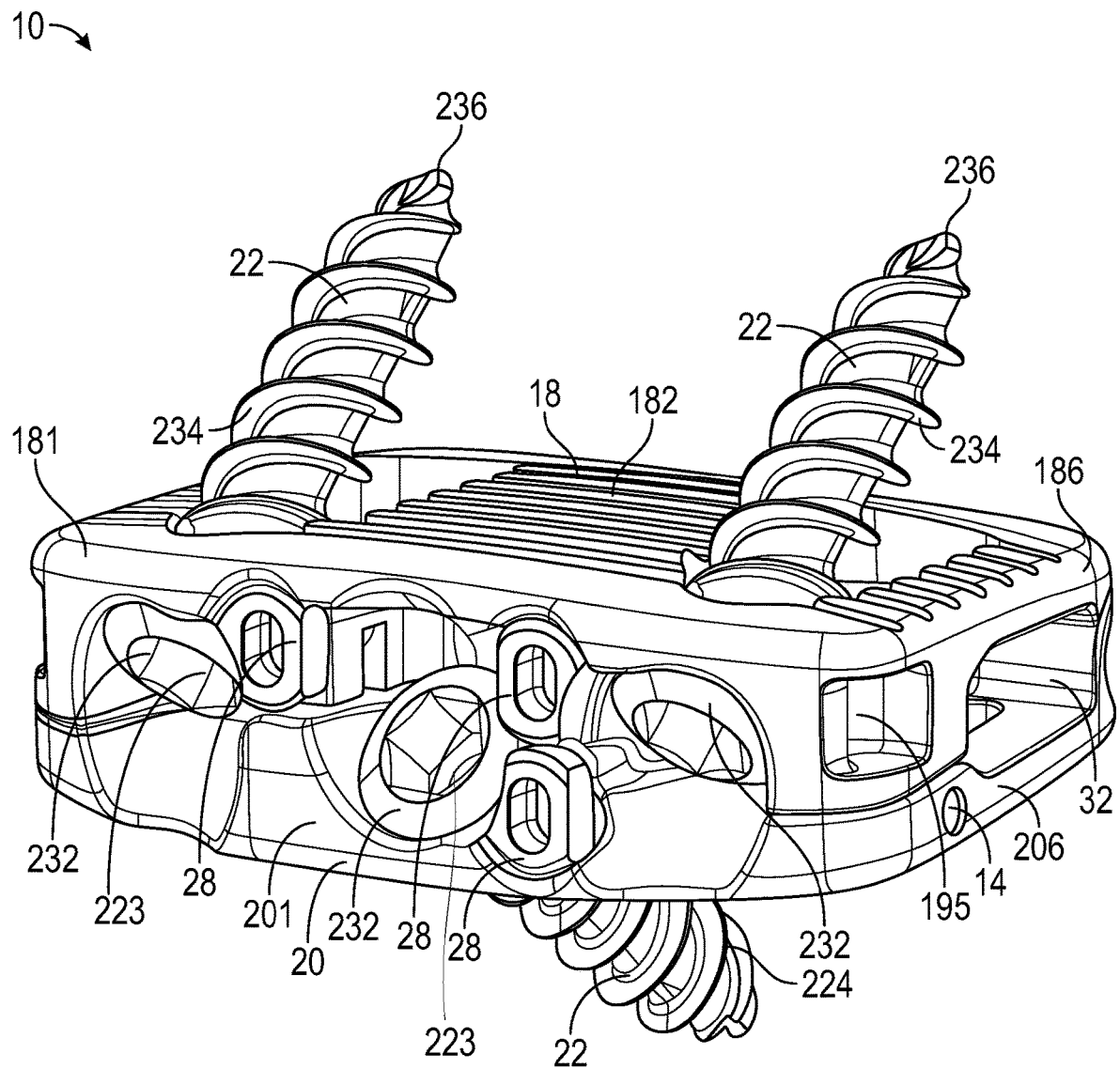
FIG. 1 is a perspective view of an implant in a first, collapsed position according to an example embodiment.

Corresponding reference characters indicate corresponding parts throughout the several views. Although the drawings represent embodiments of the disclosure, the drawings are not necessarily to scale and certain features may be exaggerated in order to better illustrate and explain the principles of the present disclosure. The exemplifications set out herein illustrate several embodiments, but the exemplifications are not to be construed as limiting the scope of the disclosure in any manner.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

The present disclosure relates to expandable and/or dynamic implants. In an example embodiment, the implant may be an interbody (between adjacent vertebrae), intravertebral-body (inside the vertebrae) and/or spinal stabilization device that may or may not be used as an interbody fusion cage or device, interbody/intravertebral body stabilization device and/or the like (e.g., spinal device(s)) for providing support, stabilization and/or promoting bone growth between or inside vertebrae or other portions of bone that have been destabilized or otherwise due to injury, illness and/or the like. Particularly, the present disclosure provides various versions of dynamic (expandable and/or expandable and retractable) interbody/intravertebral body devices that are usable in a spinal column or other areas of a human.

Various embodiments disclosed herein are directed to expandable implants that are implantable between adjacent bodies of bone. For example, the implant may be implanted or inserted into a human spine adjacent upper and lower vertebrae of the spine. According to various exemplary embodiments, the components of the implants disclosed herein may be made of any suitable material(s), including a variety of metals, plastics, composites, or other suitable bio-compatible materials. In some embodiments, one or more components of the implants disclosed herein may be made of the same material, while in other embodiments, different materials may be used for different components of the various implants.

In some embodiments, the implant described herein may be used to restore vertical disc height and accommodate the patient anatomy. For example, the dimensions and functionality of the implant may be customized based on the patient's anatomy and desired use of the implant. Further, the implant may be used to correct lordosis of the spine by adjusting the angle in situ.

Referring to the Figures generally, an expandable implant is disclosed. For example, in some embodiments, the expandable implant may be an adjustable lordosis hinged expandable fixated spinal implant. In some embodiments, the implant may include two domed, curved, or flat endplates or supports. The implant may further include pin(s) used to rotatably (e.g., pivotally, hingedly, etc.) couple the two supports to each other. For example, the two supports may be coupled to each other via a hinge mechanism at the posterior or rear portion of the implant. The implant may further include a drive screw or control driver configured to control relative movement of the two supports. The implant may further include a control member (e.g., a sliding nut or control block) configured to translate along the control driver thereby causing relative movement of the two supports. The implant may further include a linkage member or multiple linkage members coupled to the control member and one or both of the supports to facilitate controlled expansion of the two supports. The first or upper support may be rotatably coupled to the second lower support. For example, the implant may further include a linkage connection pin or multiple connection pins used to pivotally (e.g., hingedly) couple the linkage members to the upper support or the lower support. Further, the implant may be configured to receive an anchoring member or multiple anchoring members used to secure the implant into a location within the patient. Further, the implant may include a retention screw or integrated cam screw used to prevent back out of the anchoring members.

Referring now to FIGS. 1-7, an implant or expandable implant 10 is shown according to an exemplary embodiment. The implant 10 is usable, for example, between and/or within vertebral bodies of the spine. It should be understood that the implant 10 may in some embodiments be usable in other portions of the body in addition to the spine, and all such applications are to be understood to be within the scope of the present disclosure. In certain embodiments, the implant 10 may include one or more anchoring members 22, such as bone screws or bone barbs. However, in other embodiments, the implant 10 does not include any anchoring members 22.

Figure 2:
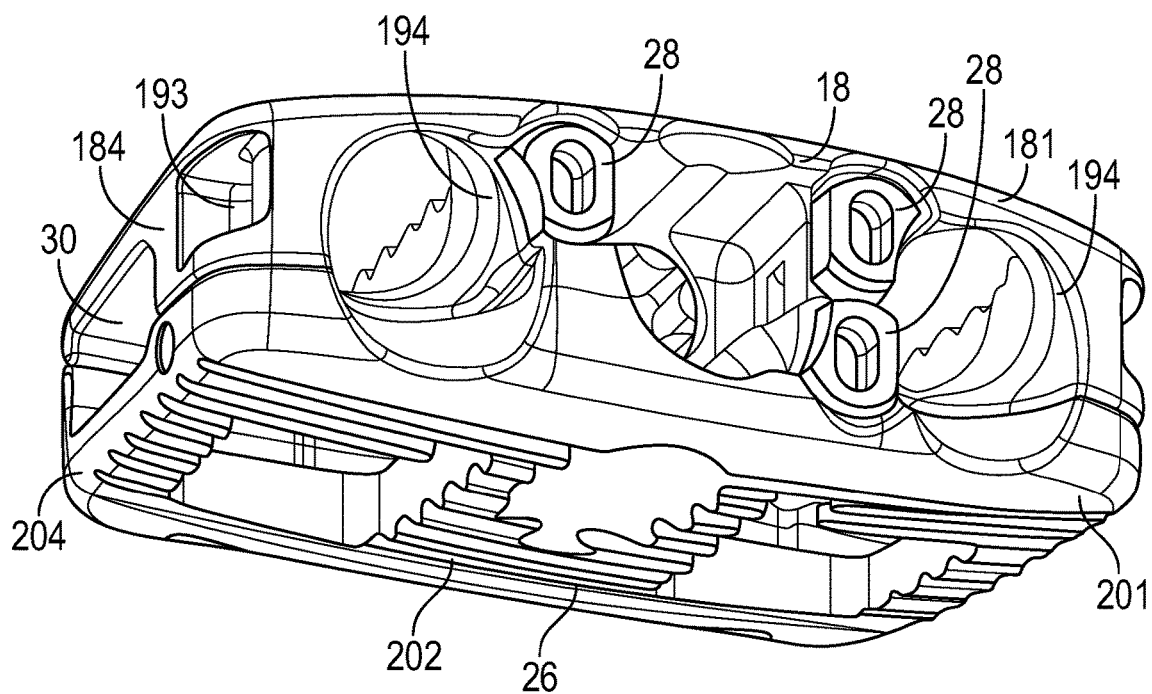
FIG. 2 is a perspective view of an implant in a first, collapsed position according to an example embodiment.
Figure 3:
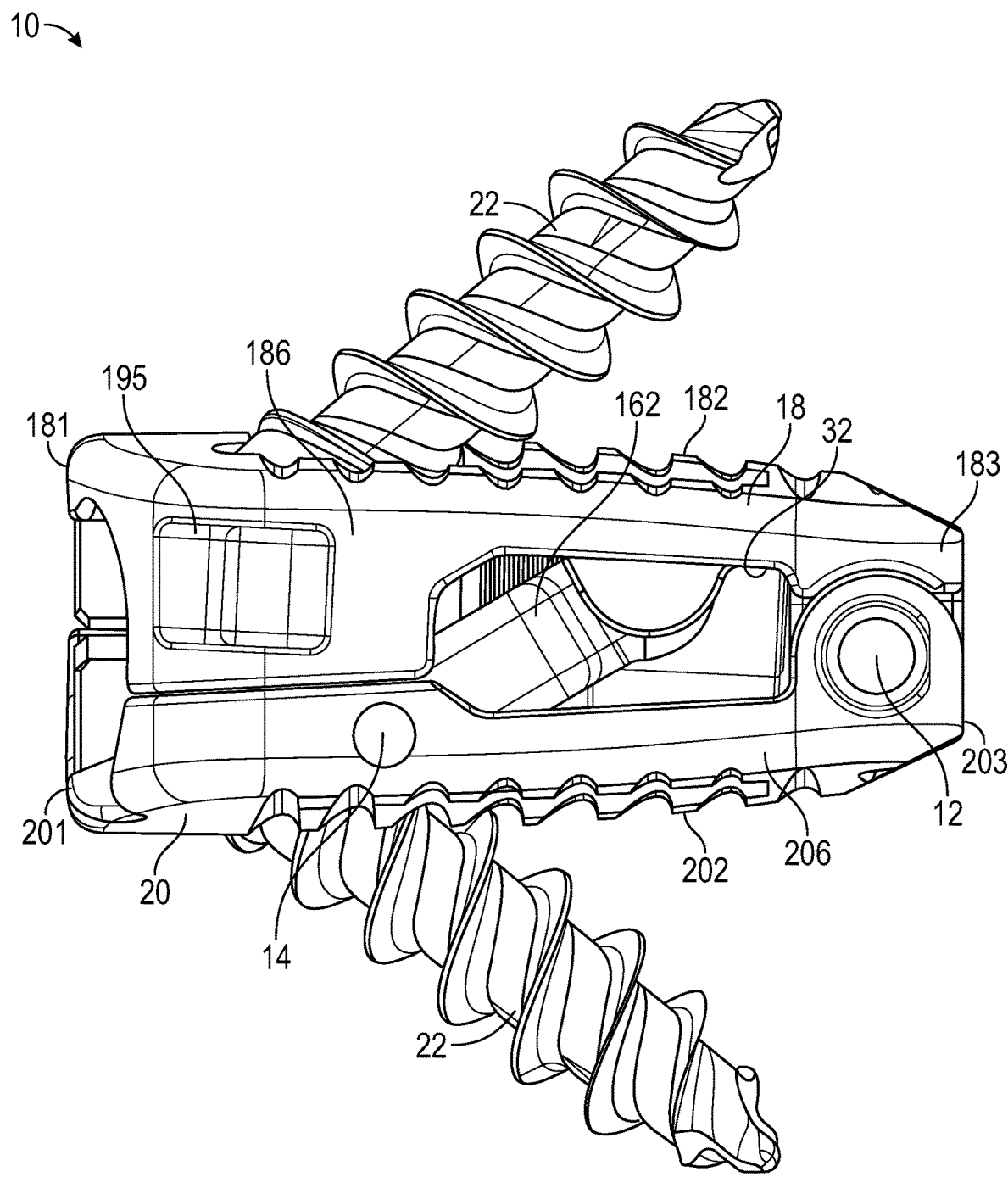
FIG. 3 is a side view of the implant of FIG. 1 according to an example embodiment.
Figure 4:
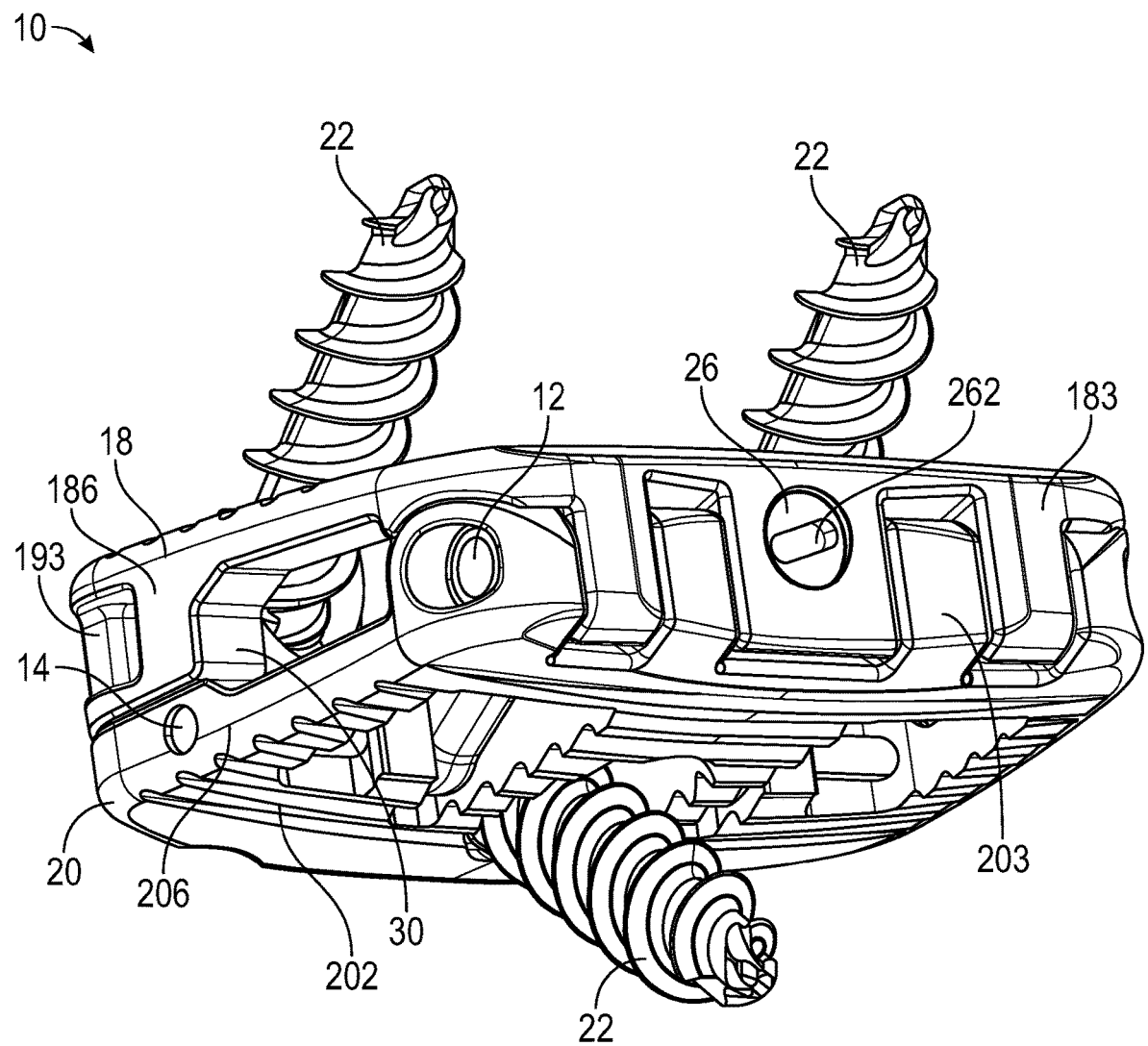
FIG. 4 is a perspective view of the implant of FIG. 1 according to an example embodiment.

As shown in FIG. 2, the first or upper support 18 may include one or more anchoring apertures 194 configured to individually receive the anchoring members 22. The anchoring members 22 may then be inserted into the anchoring apertures 194 to secure the upper support 18 in a desired location. Further, the second or lower support 20 may include one or more anchoring apertures 218 configured to individually receive the anchoring members 22. The anchoring members 22 may then be inserted into the anchoring apertures 218 to secure the lower support 20 in a desired location.

The anchoring members 22 may be bone screws, such as shown in FIG. 1. The anchoring members 22 may include a head 232, a threaded shaft 234, and a tip 236 opposite the head 234. The head 232 may further include an expansion tool interface 223 configured to receive a driver (e.g., a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver) used to screw the anchoring members 22 into the vertebrae adjacent the implant 10.

In some embodiments, if the implant 10 includes one or more anchoring member 22 used to secure the implant 10, the implant 10 may include one or more retention members 28 used to prevent back out of the anchoring members 22. For example, as shown in FIG. 1, the upper support 18 may be configured to receive two retention members 28 and the lower support 20 may be configured to receive a retention member 28, as will be discussed further herein.

According to an exemplary embodiment, the implant 10 includes a first, or upper support 18 (e.g., an upper plate, support member, assembly, etc.) and a second, or lower support 20 (e.g., a lower plate, support member, assembly). The implant 10 may also include a control assembly 16 (see FIG. 11) that is configured to control relative movement between the upper support 18 and the lower support 20. The control assembly 16 may include one or more linkage members 162, a nut or control member 164 coupled to the linkage member(s) 162, a control retention member 26, and a control driver 166 configured to be received by the control member 164, as will be discussed further herein (see FIG. 11).

In some embodiments, such as the embodiments shown in FIGS. 1-4, the upper support 18 includes a front portion 181, a rear portion 183 opposite the front portion 181, a first lateral side 184, and a second lateral side 186 opposite the first lateral side 184. Similarly, the lower support 20 includes a front portion 201, a rear portion 203 opposite the front portion 201, a first lateral side 204, and a second lateral side 206 opposite the first lateral side 204.

Figure 5:
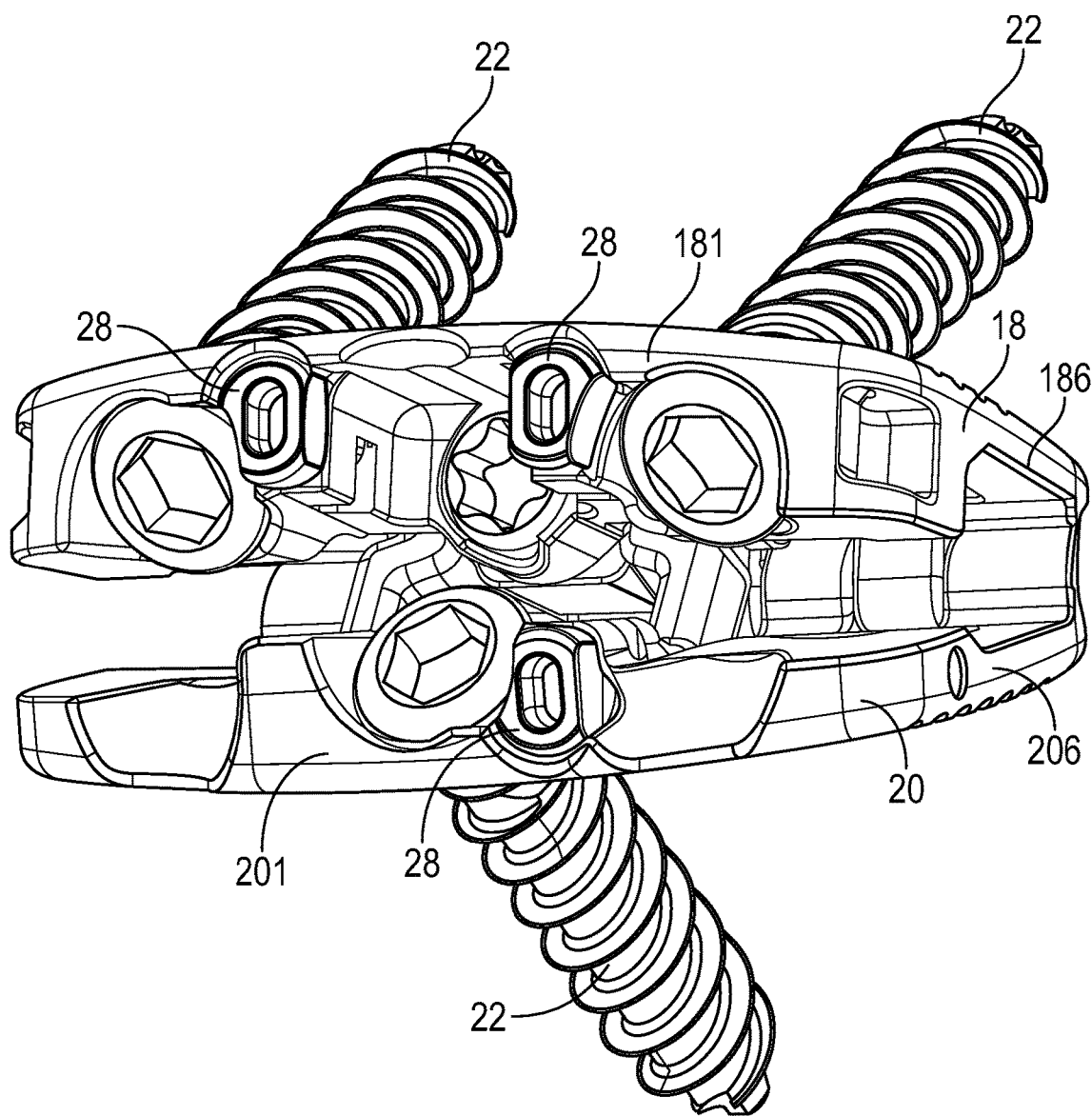
FIG. 5 is a perspective view of the implant of FIG. 1 in an expanded position according to an example embodiment.
Figure 6:
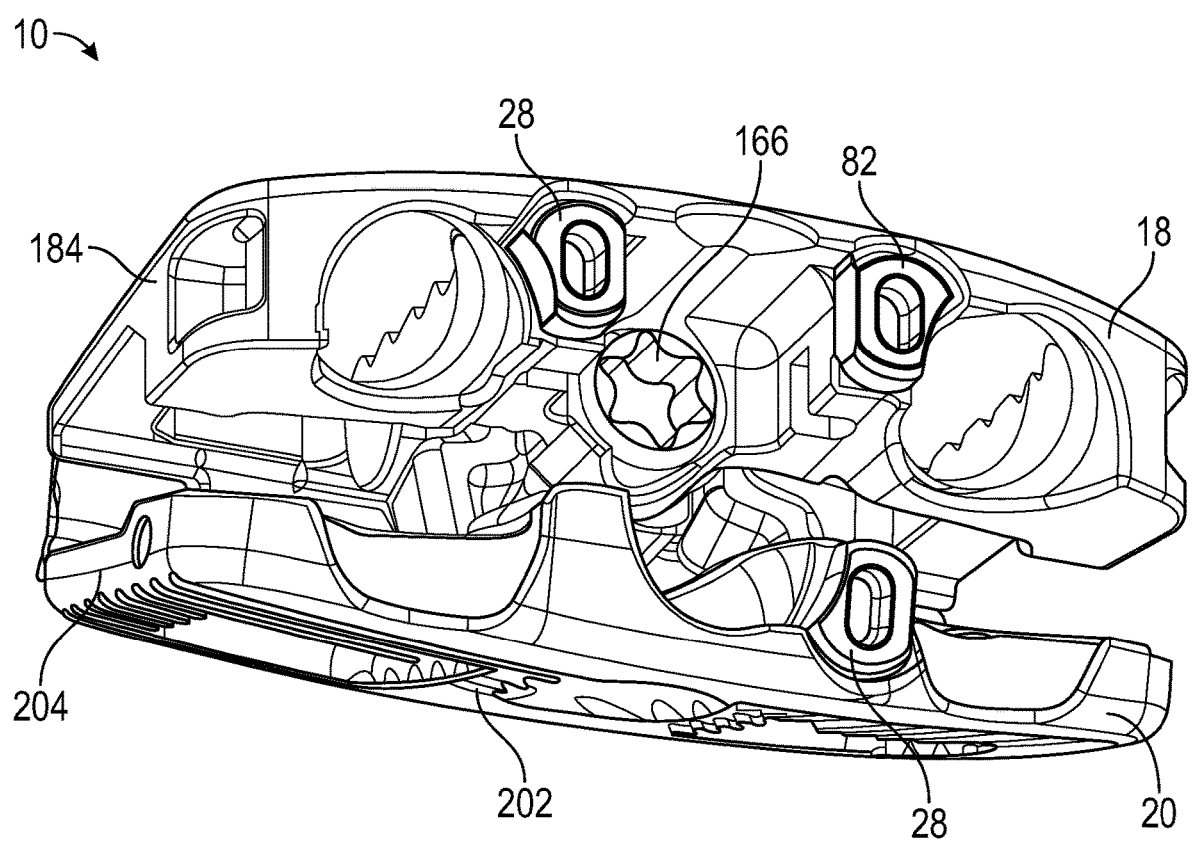
FIG. 6 is a perspective view of the implant of FIG. 2 in an expanded position according to an example embodiment.
Figure 7:
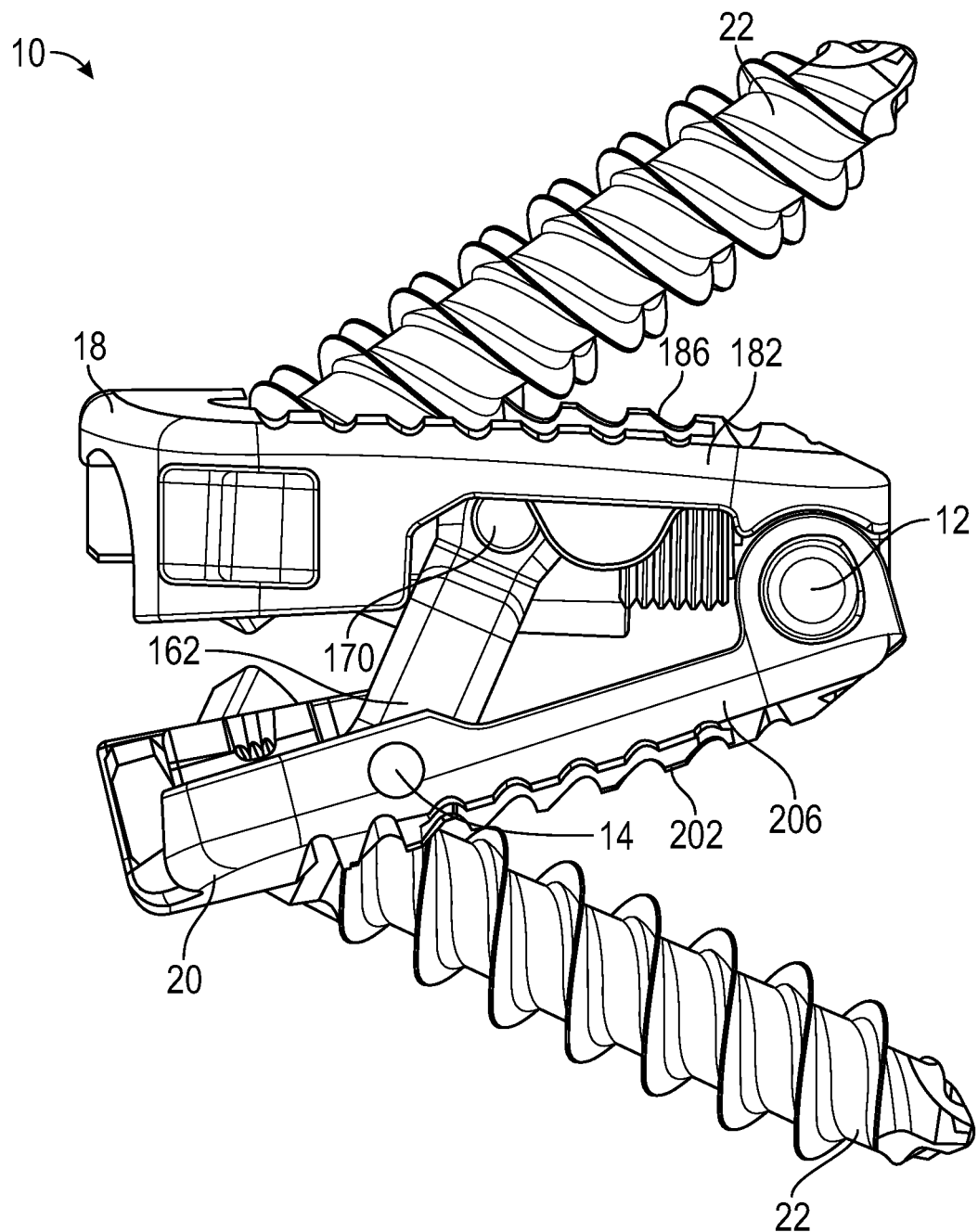
FIG. 7 is a side view of the implant of FIG. 1 in an expanded position according to an example embodiment.

According to an exemplary embodiment, the upper support 18 and the lower support 20 define a height of the implant 10 (e.g., a support height defined by the upper and lower grooved/toothed surfaces of the implant 10), wherein the height of the implant 10 is the vertical distance between the outer or top surface 182 of the upper support 18 and the outer or bottom surface 202 of the lower support 20. The height may vary throughout the implant 10. For example, if the top surface 182 of the upper support 18 and the bottom surface 202 lower support 20 are arched or curved in shape, such as shown in the example embodiment in FIG. 1, the height of the implant 10 may be smaller proximate a first lateral side 184 of the upper support 18 and a second lateral side 186 of the upper support 18 than the height proximate the lateral center of the implant 10. Further, the height may vary thought out the implant 10 due to a non-linear expansion profile. For example, as shown in FIGS. 5-7, the height proximate the front of the implant 10 (i.e., proximate the front portion 181 of the upper support 18 and proximate the front portion 201 of the lower support 20) is substantially greater than the height proximate the rear of the implant 10 (i.e., proximate the rear portion 183 of the upper support 18 and proximate the rear portion 203 of the lower support 20).

The implant 10 may include a first lateral window 30 (see FIG. 2) and a second lateral window 32 (see FIG. 1). After the implant 10 has been installed into a patient, the lateral windows 30, 32 may allow for visualization of the graft area within a central cavity of the implant 10. By aiming a medical imaging device (e.g., an x-ray machine, fluoroscope, ultrasound, MM, etc.) substantially parallel to the walls of the lateral windows 30, 32, a medical practitioner or other user is able to view the graft area through each lateral window 30, 32. Therefore, the medical practitioner can use a medical imaging device (e.g., an x-ray machine, fluoroscope, ultrasound, MM, etc.) to view the graft area through the lateral windows 30, 32. Further, the lateral windows 30, 32 reduce the overall weight of the implant 10 while still providing sufficient structural strength.

The implant 10 may be movable between at least a first, collapsed orientation and a second, expanded orientation. For example, the implant 10 is shown in the first, collapsed orientation in FIGS. 1-4. Further, the implant 10 is shown in the second, expanded orientation in FIGS. 5-7, according to an example embodiment. It should be appreciated that the first, collapsed orientation is not necessarily representative of the minimum height of the implant 10 (i.e., the first, collapsed orientation is not necessarily a fully collapsed orientation) and the second, expanded orientation is not necessarily representative of the maximum height of the implant 10 (i.e., the second, collapsed orientation is not necessarily a fully expanded orientation). Instead, the first, collapsed position may be any position wherein the average height throughout the implant 10 is less than the average height throughout the implant 10 in the second, expanded position.

Figure 8:
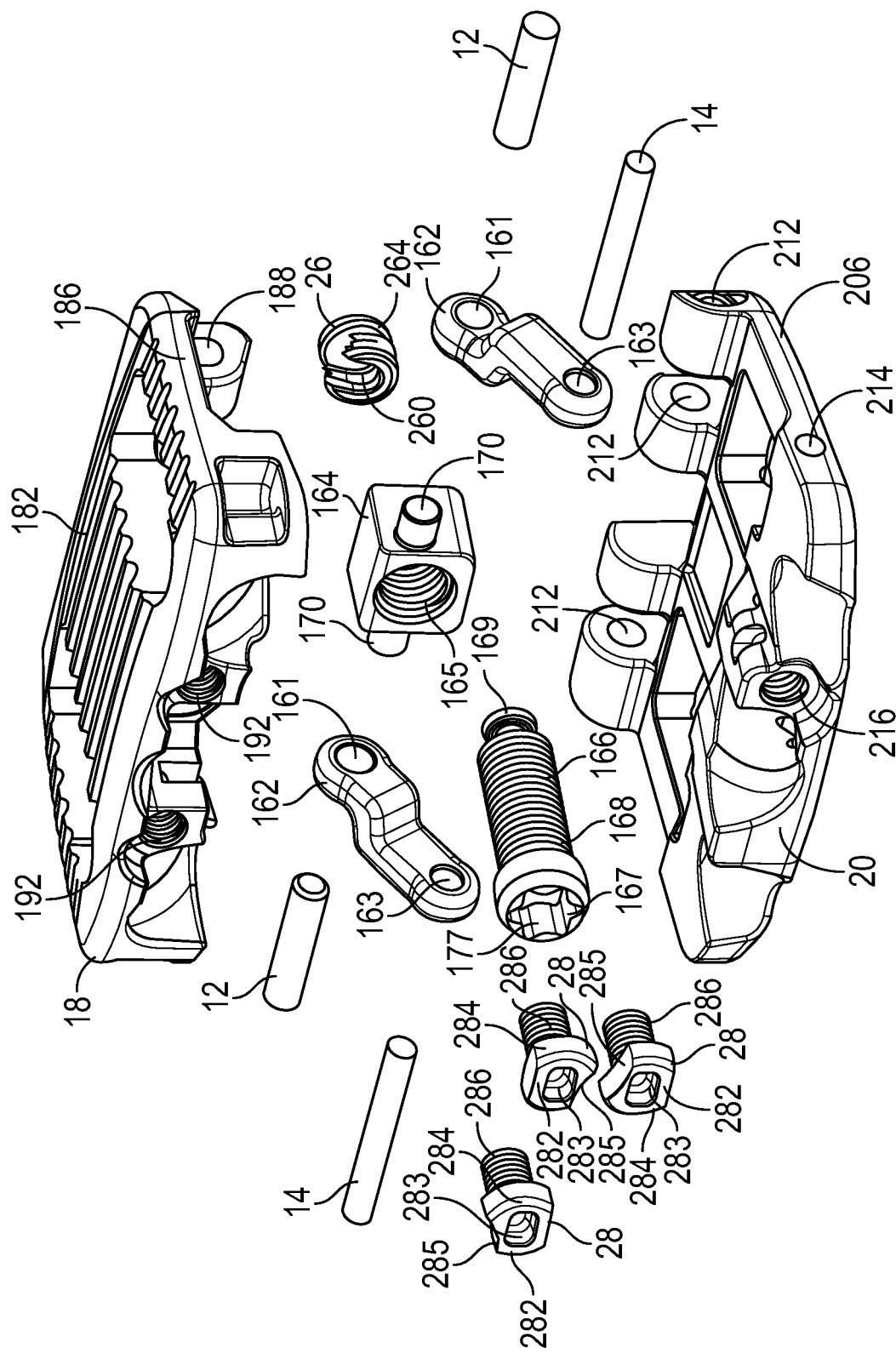
FIG. 8 is an exploded view of the implant of FIG. 2 according to an example embodiment.

Referring now to FIG. 8, an exploded view of an expandable implant 10 is shown according to an example embodiment. According to some embodiments, the implant 10 may include one or more hinge pins 12. For example, the hinge pins 12 may be used to rotatably couple (e.g., via a hinge mechanism) the upper support 18 to the lower support 20 at a distal end (e.g., proximate the rear portion 183) of the implant 10. For example, the rear portion 183 of the upper support 18 may interface with the rear portion 203 of the lower support 20 such that a first hinge pin aperture 212 of the lower support 20 (e.g., the hinge pin aperture 212 proximate the first lateral side 204 of the lower support 20) aligns with a first hinge pin aperture 188 of the upper support 18 (e.g., the hinge pin aperture 188 proximate the first lateral side 184 of the upper support 18) and a second hinge pin aperture 212 of the lower support 20 (e.g., the hinge pin aperture 212 proximate the second lateral side 206 of the lower support 20) aligns with a second hinge pin aperture 188 of the upper support 18 (e.g., the hinge pin aperture 188 proximate the second lateral side 186). A first hinge pin 12 and a second hinge pin 12 may then be inserted (e.g., pressure fit, friction fit, etc.) into the hinge pin apertures 188, 212 of the upper support 18 and the lower support 20, respectively, such that the upper support 18 is hingedly coupled to the lower support 20 (i.e., the upper support 18 and the lower support 20 may rotate about the hinge pins 12). It should be appreciated that the implant 10 includes two hinge pins 12 for additional stability, however, other implants may only include one hinge pin 12.

According to some embodiments, implant 10 may include one or more linkage pins 14. For example, the linkage pins 14 may be used to hingedly couple the linkage member(s) 162 to the lower support 20. For example, lower support 20 may include a first linkage pin aperture 214 (e.g., the linkage pin aperture 214 proximate the first lateral side 204 of the lower support 20) and a second linkage pin aperture 214 (e.g., the linkage pin aperture 214 proximate the second lateral side 206 of the lower support 20). The first linkage pin aperture 214 may align with a second linkage aperture 163 of a first linkage member 162, such that a first linkage pin 14 may be inserted (e.g., pressure fit, friction fit, etc.) into the first linkage pin aperture 214 and the second linkage aperture 163 of the first linkage member 162 to hingedly couple the first linkage member 162 to the lower support 20 so that the first linkage member 162 may rotate about the first linkage pin 14. Similarly, the second linkage pin aperture 214 may align with the second linkage aperture 163 of the second linkage member 162, such that a second linkage pin 14 may be inserted (e.g., pressure fit, friction fit, etc.) into the second linkage pin aperture 214 to hingedly couple the second linkage member 162 to the lower support 20 and the second linkage aperture 163 of the second linkage member 162 to hingedly couple the second linkage member 162 to the lower support 20 so that the second linkage member 162 may rotate about the second linkage pin 14. It should be appreciated that the implant 10 includes two linkage members 162 and two linkage pins 14 for additional stability, however, other implants may only include one linkage member 162 and one linkage pin 14.

According to some example embodiments, the implant 10 includes a control assembly 16. For example, the control assembly 16 may be configured to control relative movement between the upper support 18 and the lower support 20. The control assembly may include a control driver 166. The control driver 166 may include a head 167, a shaft 168, and a tip 169. The head 167 may include an expansion tool interface 177 configured to receive an expansion tool, such as shown in FIG. 8. In this example embodiment, an expansion tool, such as a torx driver, may be used to manipulate the control driver 166 to control relative movement between the upper support 18 and the lower support 20. While this example embodiment shows the expansion tool interface 177 as being a torx head socket, it should be appreciated that the expansion tool interface 177 can be designed to receive several different types of tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

In some example embodiments, the shaft 168 may be configured to be received by a control bore 165 within the control member 164. For example, the shaft 168 of the control driver 166 and the control bore 165 of the control member 164 are threaded such that manipulation (e.g., rotation) of the control driver 166 causes the control member 164 to translate along the shaft 168 of the control driver 166, thereby causing relative movement between the upper support 18 and the lower support 20, as will be discussed further herein. It should be appreciated that, while the Figures generally show the control bore 165 of the control member 164 threadingly engaging the shaft 168 of the control driver 166, in other embodiments, other adjustment mechanisms may be used (e.g., ratchet mechanisms, indents/detents, etc.). In these embodiments, the control driver 166 may be manipulated (e.g., urged, turned, pushed, rotated, etc.) to control relative movement between the upper support 18 and the lower support 20.

In certain embodiments, the control member 164 may include one or more linkage protrusions 170 that may be used to couple the control member 164 to the one or more linkage members 162. For example, the linkage members 162 may include a first linkage aperture 161 configured to receive the linkage protrusion 170. The linkage protrusion 170 may be inserted (e.g., pressure fit, friction fit, etc.) into the first linkage aperture 161 to hingedly couple the linkage member 162 to the control member 164 such that the linkage member 162 may rotate about the linkage protrusion 170. It should be appreciated that the implant 10 includes two linkage members 162 and two linkage protrusions 170 for additional stability, however, other implants may only include one linkage member 162 and one linkage protrusion 170.

In some embodiments, the control driver 166 may also include a tip 169. Further, the tip 169 may be configured to be received by a retention interface 260 of the control retention member 26. For example, as shown in FIG. 8, the tip 169 may include a shoulder that allows the control driver 166 to be coupled to the control retention member 26 via a shoulder slot in the retention interface 260. As shown, the retention interface 260 includes a horseshoe slot configured to receive the rounded shoulder of the tip 169 of the control driver 166. As will be discussed further below, the control retention member 26 may be secured to the implant 10. For example, the control retention member 26 may include a threaded shaft 264 that may engage a first bore 185 (e.g., a control retention aperture) (see FIG. 9) proximate the rear portion 183 of the upper support 18. In certain embodiments, the first bore 185 may be threaded. Thus, the tip 169 of the control diver 166 may be coupled to the retention interface 260 of the control retention member 26, and the control retention member 26 may be secured within the first bore 185 of the upper support 18, thereby securing the control assembly 16 within the implant 10.

As discussed above, the implant 10 may include one or more retention members 28 used to prevent back out of the anchoring members 22. As shown in FIG. 8, the retention members 28 include a head 282 and a shaft 286. The head 282 further includes an expansion tool interface 283, a rounded portion 284, and a cutout section 285. The expansion tool interface 283 may be configured to receive a tool that may be used to tighten and/or loosen the retention members 28. While the expansion tool interface 283 shown is configured to receive a specialized tool, the expansion tool interface 283 may be configured to receive several different types of tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

In some example embodiments, the shaft 286 of the retention member 28 may by threaded such that it may be screwed into a threaded retention aperture 192 in the upper support 18 and/or a threaded retention aperture 216 of the lower support 20. In certain embodiments, the retention members 28 may be pre-threaded into the threaded retention apertures 192, 216 prior to inserting the implant 10 into a patient. For example, the retention members 28 may be pre-threaded into a first position, such as the position shown in FIG. 2. When the retention member 28 is in the first position, the cutout section 285 of the retention member 28 may provide sufficient clearance such that the anchoring member 22 may be inserted into the anchoring apertures 194, 218. Once the anchoring members 22 are inserted, the retention member 28 may be turned to a second position (e.g., screwed in using a specialized tool designed to engage the expansion tool interface 283) such that the rounded portion 284 reduces the clearance of the anchoring apertures 194, 218 to prevent back out of the anchoring members 22. For example, the rounded portion 284 may engage the head 282 of the anchoring member 22, thereby preventing back out of the anchoring member 22.

Figure 9:
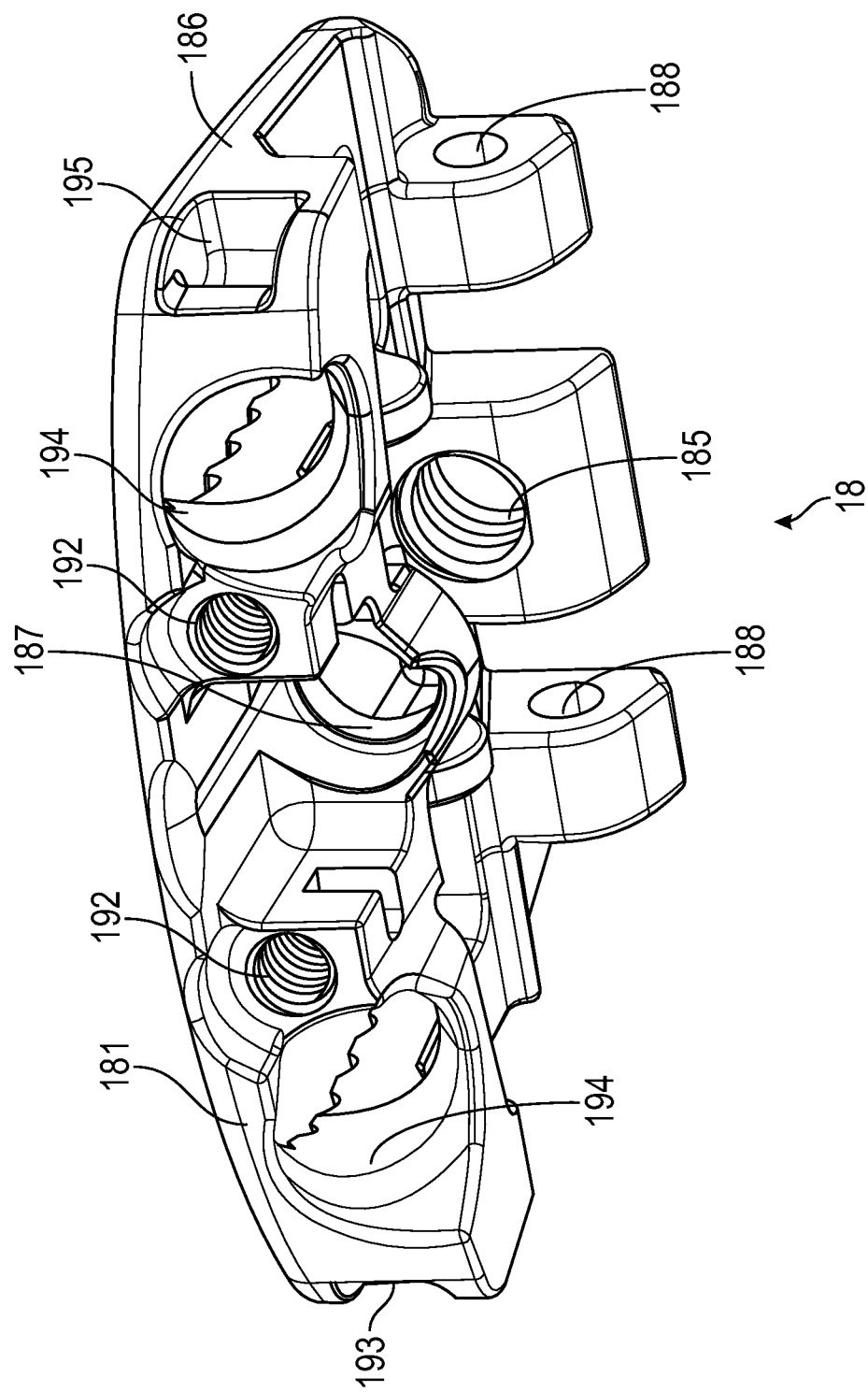
FIG. 9 is a perspective view of an upper support according to an example embodiment.

Referring now to FIG. 9, the upper support 18 is shown according to an example embodiment. According to an example embodiment, the upper support 18 includes a first bore 185 and a second bore 187 configured to secure the control assembly 16. For example, the control driver 166 may be inserted into the second bore 187 such that the shaft 168 may rotate within the second bore 187. Further, the tip 169 may be positioned within the first bore 185, such that the control retention member 26 may be used to secure the control driver 166 such that the tip 169 may rotate within the retention interface 260.

In some example embodiments, the upper support 18 and/or the lower support 20 may include one or more installation tool interfaces 193, 195. For example, as shown in FIG. 9, the implant 10 may include a first installation tool interface 193 proximate the first lateral side 184 (see FIG. 2). The implant 10 may further include a second installation tool interface 195 proximate the second lateral side 186. The first and second installation tool interfaces 193, 195 may be utilized with an installation tool to assist a medical practitioner or other user in inserting the implant 10 into a patient. For example, the installation tool may controllably grip (e.g., pinch, squeeze, etc.) the installation tool interfaces 193, 195 to secure the implant 10 to the installation tool. The installation tool may then be used to insert the implant 10 into a patient and once the implant 10 is in a desired location, the operator may controllably release the implant 10 from the installation tool.

Figure 10:
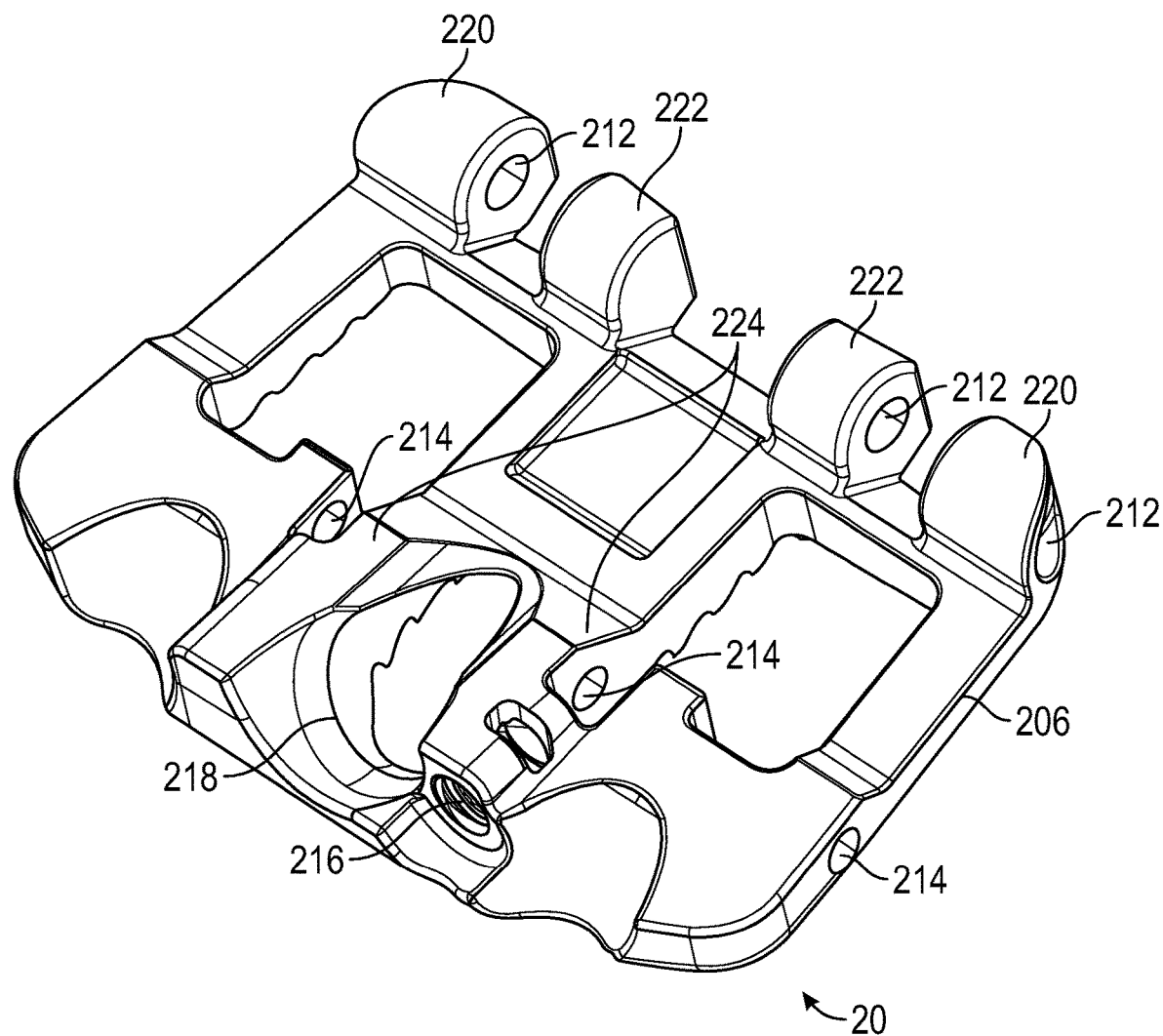
FIG. 10 is a perspective view of a lower support according to an example embodiment.

Referring now to FIG. 10, the lower support 20 is shown according to an example embodiment. As discussed above, the lower support 20 includes a first hinge pin aperture 212 (e.g., the hinge pin aperture 212 proximate the first lateral side 204 of the lower support 20) and a second hinge pin aperture 212 (e.g., the hinge pin aperture 212 proximate the second lateral side 206 of the lower support 20). In this example embodiment, the hinge pin apertures 212 extend from the lateral sides 204, 206, through a first hinge portion 220 and into a second hinge portion 222. However, in other embodiments, the hinge pin apertures 212 may not extend into the second hinge portion 222.

As discussed above, the lower support 20 includes a first linkage hinge aperture 214 (e.g., the linkage hinge aperture 214 proximate the first lateral side 204 of the lower support 20) and a second linkage hinge aperture 214 (e.g., the linkage hinge aperture 214 proximate the second lateral side 206 of the lower support 20). In this example embodiment, the hinge pin apertures 212 extend from the lateral sides 204, 206 and a central portion 224 of the lower support 20.

However, in other embodiments, the linkage hinge apertures 214 may not extend into the central portion 224.

Figure 11:
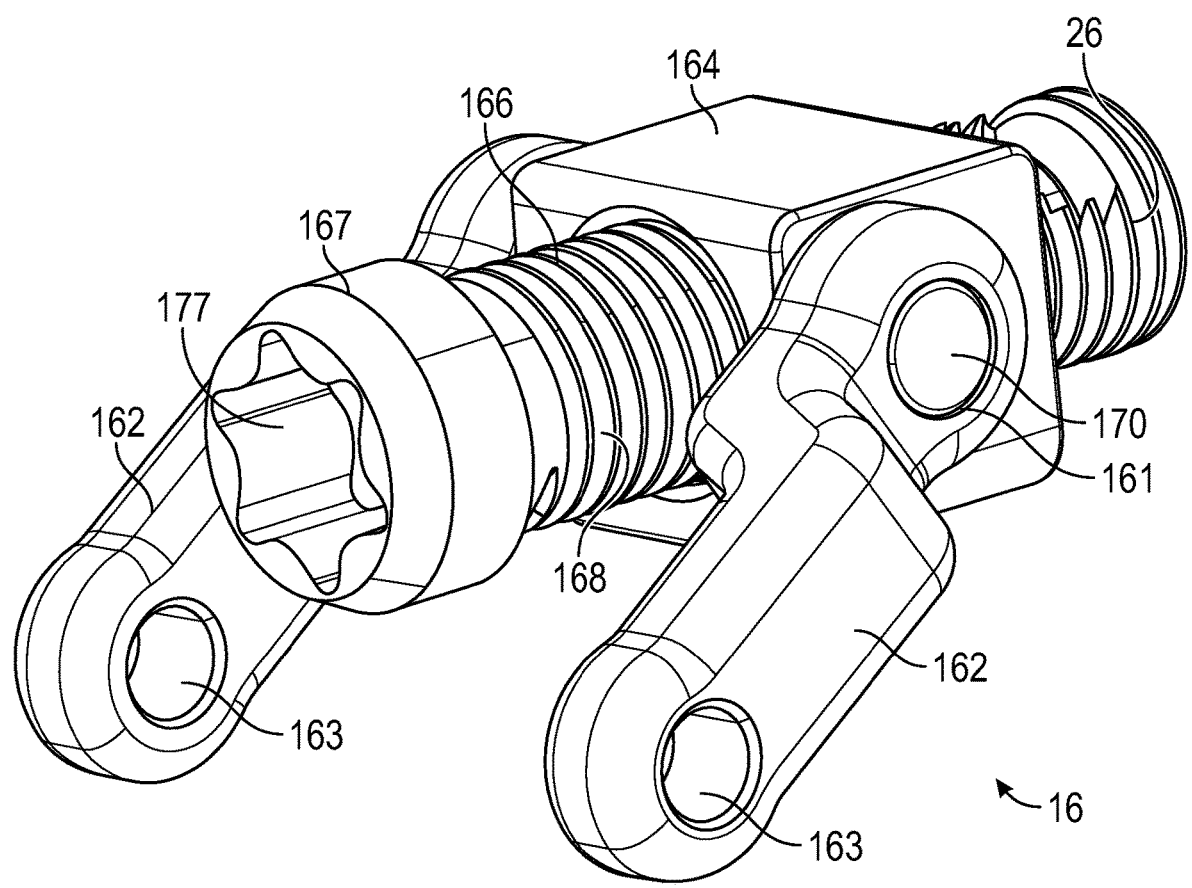
FIG. 11 is a perspective view of a control assembly according to an example embodiment.

Referring now to FIG. 11, the control assembly 16 is shown in an example embodiment. The control assembly 16 may include one or more linkage members 162, a nut or control member 164 coupled to the linkage member(s) 162, a control retention member 26, and a control driver 166 configured to be received by the control member 164. The control assembly 16 may include a control driver 166. The control driver 166 may include a head 167, a shaft 168, and a tip 169. The head 167 may include an expansion tool interface 177 configured to receive an expansion tool. In this example embodiment, an expansion tool, such as a torx driver, may be used to manipulate the control driver 166 to control relative movement between the upper support 18 and the lower support 20. While this example embodiment shows the expansion tool interface 177 as being a torx head socket, it should be appreciated that the expansion tool interface 177 can be designed to receive several different types of tools, including a slotted screwdriver, a Phillips-head screwdriver, an Allen wrench screwdriver, a hexagonal drive, a torx drive, a Robertson drive, a tri-wing screwdriver, an Allen security driver, a torx security driver, a Pozidriv, a clutch drive, a spanner, a Schrader drive, a nut driver, a hex wrench, a node security driver, any combination of the listed driver interfaces, and any other type of driver interface.

As discussed above, the shaft 168 of the control driver 166 may be received by the control member 164. For example, the shaft 168 may threadingly engage a central bore 165 (see FIG. 8) of the control member 164. For example, the shaft 168 of the control driver 166 and the control bore 165 of the control member 164 are threaded such that manipulation (e.g., rotation) of the control driver 166 causes the control member 164 to translate along the shaft 168 of the control driver 166. In use, as the control member 164 translates along the shaft 168, the upper support 18 and the lower support 20 will move relative to one another due to the linkage members 162 being hingedly attached to the control member 164, the linkage members 162 also being hingedly attached to the lower support 20, and the control driver 166 being coupled to the upper support 18 via the first bore 185 and the second bore 187 (see FIG. 9). For example, as the control member 164 translates towards the front portion 181 of the upper support 18 (see FIG. 1), the upper support 18 may expand away from the lower support 20.

Figure 12:
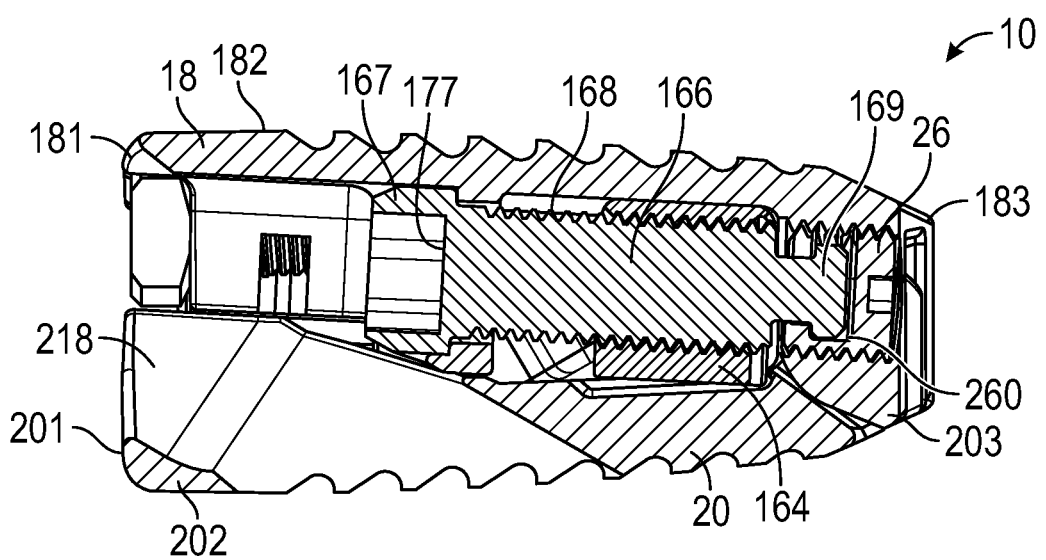
FIG. 12 is a cross-sectional view of the implant of FIG. 2 according to an example embodiment.
Figure 13:
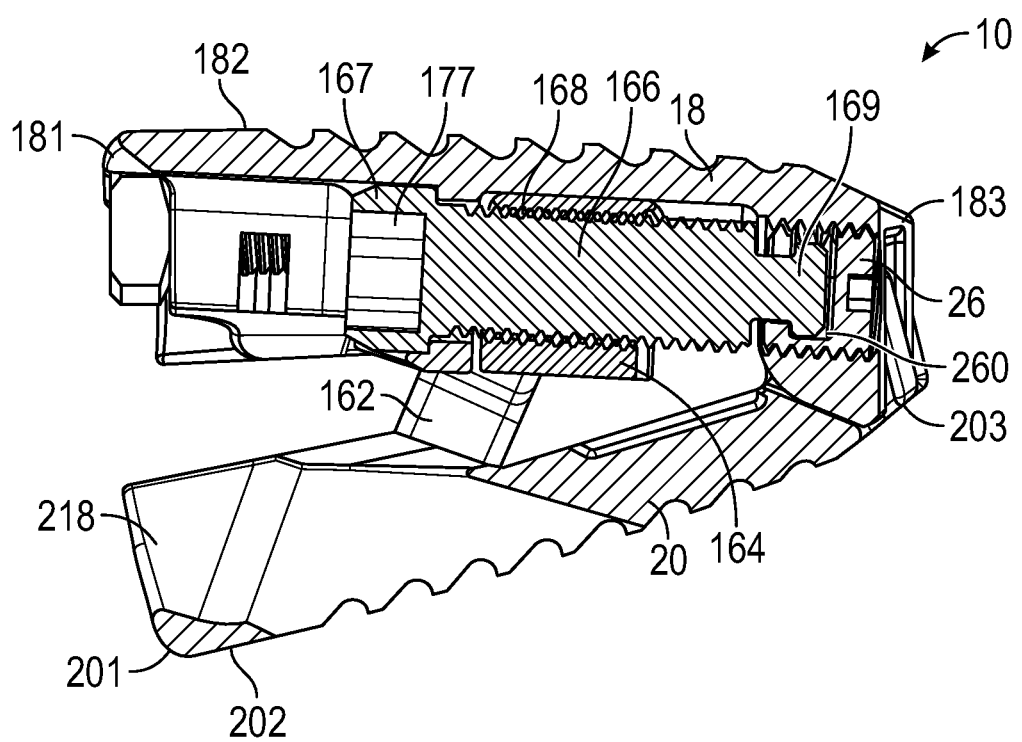
FIG. 13 is a cross-sectional view of the implant of FIG. 6 according to an example embodiment.

Referring now to FIGS. 12 and 13, cross-sectional views of the implant 10 are shown according to an example embodiment. In this example embodiment, the implant 10 is shown without anchoring members 22, however, in other embodiments, the implant 10 may include one or more anchoring members 22. FIG. 12 shows the implant 10 in a first, collapsed orientation and FIG. 13 shows the implant 10 in a second, expanded orientation. In these example embodiments, the control driver 166 may be used to control relative movement between the upper support 18 and the lower support 20. The tip 169 of the control driver 166 is positioned within the control retention interface 260 of the control retention member 26, such that the tip 169 may rotate within the control retention interface 260. As the control driver 166 is manipulated (e.g., rotated using a torx head driver), the control member 164 may translate along the shaft 168 of the control driver 166. As the control member 164 translates from the position shown in FIG. 12 to the position shown in FIG. 13, the angle formed by the top surface 182 of the upper support 18 and the bottom surface 202 of the lower support 20 increases. Further, the average height throughout the implant 10 (i.e., the height of the implant 10 is the vertical distance between the outer or top surface 182 of the upper support 18 and the outer or lower surface 202 of the lower support 20) increases as the control member 164 translates from the position shown in FIG. 12 to the position shown in FIG. 13. However, due to the hinged connection proximate the rear portion 183 of the upper support 18 and the rear portion 203 of the lower support 20, the height at the rear of the implant 10 remains substantially the same relative to the change in height near the front of the implant 10 (i.e., proximate the front portion 181 of the upper support 18 and the front portion 201 of the lower support 20). Therefore, as the control driver 166 is manipulated and the control member 164 translates towards the front of the implant 10, the rate of change of the height is greater proximate the front of the implant 10 than proximate the rear of the implant 10.

Referring now to the Figures generally, the various embodiments disclosed herein provide expandable implants including a lower support and an upper support adjustably coupled to the lower support and movable between a first, collapsed position, and a second, expanded position.

In some embodiments, one or both of the lower support and the upper support include projections/grooves to provide a gripping surface intended to facilitate gripping adjacent portions of bone. In further embodiments, one or both of the lower support and the upper support include one or more apertures and/or cavities configured to promote bone growth in and around the lower support and the upper support. In some embodiments, the apertures extend from a top, bottom, and/or side surface of the lower support and the upper support and to a central cavity of the implant.

According to any of the embodiments disclosed herein, one or more bone screws may be included and positioned to extend through one or both of the lower support and the upper support and into adjacent portions of bone. In some embodiments, multiple bone screws are used. A first bone screw may extend through the adjustable member and into a first portion of bone, and a second bone screw may extend through the base member and into a second portion of bone. In further embodiments, multiple bone screws are accessible and manipulatable by way of the front face of the implant defined by one or both of the adjustable member and the base member. A head and expansion tool interface of the control shaft may further be accessible by way of the front face of the implant.

In various embodiments, any suitable configuration of the control shaft/control member(s)/control channel(s) may be utilized. In some embodiments, an at least partially spherical control member threadingly engages a threaded control shaft and translates both along the control shaft. In other embodiments, the control member is non-spherical.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of some features described and claimed without restricting the scope of these features to the precise numerical ranges provided. Accordingly, these terms should be interpreted as indicating that insubstantial or inconsequential modifications or alterations of the subject matter described and claimed are considered to be within the scope of the application as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "upper," "lower," etc.) are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variations may depend, for example, on hardware systems chosen and on designer choice. All such variations are within the scope of the disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present application.

It should be appreciated that dimensions of the components, structures, and/or features of the present implants and installation instruments may be altered as desired within the scope of the present disclosure.

What is claimed is:

1. An implant, comprising:
    a first support;
    a second support coupled to the first support; and
    a control assembly configured to move the implant between at least a first, collapsed orientation and a second, expanded orientation, the control assembly comprising:
        a control driver coupled to the first support and comprising a head and a shaft, the control driver configured to control relative movement between the first support and the second support;
        a control member configured to move along the shaft of the control driver; and
        a first linkage comprising a first end pivotally coupled to the control member and a second end pivotally coupled to the second support such that the first end rotates about a first axis extending through the control member and the second end rotates about a different second axis extending through the second support and the second end of the first linkage, wherein movement of the control member causes the first support to rotate relative to the second support;
        wherein a distance between the first axis and the second axis remains constant as the first and second ends rotate about the first and second axes.

2. The implant of claim 1, wherein the first support is pivotally coupled to the second support via a hinge.

3. The implant of claim 1, wherein the control member comprises a first protrusion, and translation of the control member along the shaft of the control driver further causes the first linkage to rotate about the first protrusion.

4. The implant of claim 3, further comprising a second linkage comprising a second end pivotally coupled to the second support and a first end pivotally coupled to a second protrusion of the control member, wherein translation of the control member along the shaft of the control driver further causes the second linkage to rotate about the second protrusion.

5. The implant of claim 1, wherein the first support is configured to receive a first anchoring member and the second support is configured to receive a second anchoring member.

6. The implant of claim 1, wherein the first support comprises a top surface and the second support comprises a bottom surface;
    wherein a distance between the top surface and the bottom surface defines a height; and
    wherein translation of the control member causes a greater change in height proximate a front portion of the implant than a rear portion of the implant.

7. The implant of claim 6, wherein the first support further comprises a control retention aperture configured to receive a control retention member, wherein the control retention member includes a retention interface configured to receive a tip of the control driver.

8. The expandable implant of claim 1, wherein the control driver is translationally fixed relative to the first support.

9. The expandable implant of claim 1, wherein movement of the control driver relative to the first support is limited to rotation of the control driver about a longitudinal axis of the control driver.

10. An implant, comprising:
    an upper support;
    a lower support coupled to the upper support and configured to rotate relative to the upper support; and
    a control assembly configured to expand the implant between at least a first, collapsed orientation and a second, expanded orientation, the control assembly comprising a control member and a first linkage coupling the control member to the lower support, the first linkage comprising a first end configured to rotate about a first axis extending through the control member, and a second end configured to rotate about a second axis different from the first axis and extending through the lower support and the second end of the first linkage, wherein manipulation of the control assembly causes movement of the first linkage relative to the upper support and the lower support;

wherein a distance between the first axis and the second axis remains constant as the first and second ends rotate about the first and second axes.

11. The implant of claim 10, wherein the control member comprises a first protrusion, and translation of the control member along a shaft of a control driver further causes the first linkage to rotate about the first protrusion.

12. The implant of claim 11, further comprising a second linkage coupled to the lower support and a second protrusion of the control member, the second linkage comprising a first end configured to rotate about the first axis, and a second end configured to rotate about the second axis, wherein the translation of the control member along the shaft of the control driver further causes the second linkage to rotate about the second protrusion.

13. The implant of claim 11, wherein the upper support is configured to receive a first anchoring member and the lower support is configured to receive a second anchoring member.

14. The implant of claim 11, further comprising:
a front portion and a rear portion,
wherein the upper support comprises a top surface and the lower support comprises a bottom surface;
wherein a distance between the top surface and the bottom surface defines a height; and
wherein the height in the second, expanded position proximate the front portion of the implant is substantially greater than the height in the first, collapsed position proximate the front portion of the implant.

15. The implant of claim 11, further comprising:
a front portion and a rear portion;
wherein the upper support comprises a top surface and the lower support comprises a bottom surface;
wherein a distance between the top surface and the bottom surface defines a height; and
wherein translation of the control member causes a greater change in height proximate the front portion of the implant than the rear portion of the implant.

16. The implant of claim 15, wherein the upper support further comprises a control retention aperture configured to receive a control retention member, wherein the control retention member includes a retention interface configured to receive a tip of the control driver.

17. An expandable implant comprising:
an upper support having a top surface configured to engage a first portion of bone;
a lower support having a bottom surface configured to engage a second portion of bone, the lower support hingedly coupled to the upper support at a rear portion of the expandable implant, wherein the top surface of the upper support and the bottom surface of the lower support define an angle; and
a control assembly comprising a control driver, a linkage, and a control member, the linkage rotating about a first axis extending through the control member and a second axis different from the first axis and extending through the lower support and the linkage, the control assembly configured to control movement between the upper support and the lower support between at least a first, collapsed orientation and a second, expanded orientation, wherein manipulation of the control assembly causes the angle to change and the linkage to rotate relative to the control member and the lower support;
wherein a distance between the first axis and the second axis remains constant as the linkage rotates.

18. The expandable implant of claim 17, wherein a distance between the top surface of the upper support and the bottom surface of the lower support defines a height, wherein the manipulation of the control assembly causes a change in height proximate a front portion of the expandable implant without causing a substantial change in height proximate the rear portion of the expandable implant.

19. The expandable implant of claim 18, wherein:
the control driver is configured to be received by a first aperture in the upper support; and
the control member is configured to translate along a shaft of the control driver.

20. The expandable implant of claim 19, further comprising a control retention member configured to be threadingly received by a second aperture in the upper support, wherein the control retention member includes a retention interface configured to receive a tip of the control driver.

* * * * *